US010621733B2

(12) United States Patent
Matsuoka et al.

(10) Patent No.: US 10,621,733 B2
(45) Date of Patent: Apr. 14, 2020

(54) ENHANCED VISUALIZATION OF BREATHING OR HEARTBEAT OF AN INFANT OR OTHER MONITORED SUBJECT

(71) Applicant: Google LLC, Mountain View, CA (US)

(72) Inventors: Yoky Matsuoka, Los Altos Hills, CA (US); Shwetak Patel, Seattle, WA (US); Michael Dixon, Sunnyvale, CA (US)

(73) Assignee: Google LLC, Mountain View, CA (US)

( * ) Notice: Subject to any disclaimer, the term of this patent is extended or adjusted under 35 U.S.C. 154(b) by 88 days.

(21) Appl. No.: 15/859,640

(22) Filed: Dec. 31, 2017

(65) Prior Publication Data

US 2019/0206062 A1     Jul. 4, 2019

(51) Int. Cl.
*G06T 7/246*     (2017.01)
*A61B 5/00*     (2006.01)
(Continued)

(52) U.S. Cl.
CPC ............ *G06T 7/246* (2017.01); *A61B 5/0022* (2013.01); *A61B 5/0077* (2013.01); *A61B 5/0205* (2013.01); *A61B 5/113* (2013.01); *A61B 5/1128* (2013.01); *A61B 5/1135* (2013.01); *A61B 5/4806* (2013.01); *A61B 5/743* (2013.01); *A61B 5/744* (2013.01); *G06K 9/00342* (2013.01); *G06K 9/00711* (2013.01); *G06T 3/4069* (2013.01); *A61B 5/0046* (2013.01); *A61B 5/02427* (2013.01); *A61B 5/0816* (2013.01); *A61B 5/6898* (2013.01); *A61B 5/725* (2013.01); *A61B 5/7264* (2013.01); *A61B 5/747* (2013.01); *A61B 2503/04* (2013.01); *A61B 2576/00* (2013.01); *A61B 2576/02* (2013.01); *G06T 2207/10016* (2013.01); *G06T 2207/30076* (2013.01); *G06T 2207/30196* (2013.01);
(Continued)

(58) Field of Classification Search
CPC ... A61B 5/0022; A61B 5/0077; A61B 5/0205; A61B 5/1128; A61B 5/113; A61B 5/1135; A61B 5/4806; A61B 5/743; A61B 5/744; G06K 9/00342; G06K 9/00711; G06T 7/246; G06T 3/4069
See application file for complete search history.

(56) References Cited

U.S. PATENT DOCUMENTS 5,555,577 A    9/1996   Volpe
5,778,892 A    7/1998   Goldsmith
(Continued)

OTHER PUBLICATIONS

International Search Report and Written Opinion dated Apr. 8, 2019 in International Patent Application No. PCT/US2018/067928, all pages.

(Continued)

*Primary Examiner* — Leon Flores
(74) *Attorney, Agent, or Firm* — Kilpatrick Townsend & Stockton LLP

(57) ABSTRACT

A method of monitoring physical characteristics of subjects in sleep environments may include receiving, through a video camera, a video feed of a subject in a sleep environment; analyzing the video feed of the subject to identify motion of the subject in the video feed; and causing a mobile device to present a representation of the motion of the subject, wherein the motion of the subject is exaggerated.

16 Claims, 17 Drawing Sheets

(51) Int. Cl.
*A61B 5/113* (2006.01)
*A61B 5/0205* (2006.01)
*A61B 5/11* (2006.01)
*G06K 9/00* (2006.01)
*G06T 3/40* (2006.01)
*A61B 5/024* (2006.01)
*A61B 5/08* (2006.01)
*G08B 21/04* (2006.01)
*H04N 7/18* (2006.01)

(52) U.S. Cl.
CPC ...... *G08B 21/0415* (2013.01); *G08B 21/0476* (2013.01); *H04N 7/183* (2013.01)

(56) References Cited

U.S. PATENT DOCUMENTS

| | | |
|---|---|---|
| 5,993,397 A | 11/1999 | Branson |
| 5,996,152 A | 12/1999 | Wilson |
| 6,054,926 A | 4/2000 | Deleo |
| 6,058,939 A | 5/2000 | Goldsmith |
| 6,150,941 A | 11/2000 | Geiger et al. |
| 6,450,168 B1 | 9/2002 | Nguyen |
| 6,812,822 B1 | 11/2004 | Spector |
| 6,912,743 B1 | 7/2005 | Weil |
| 7,035,432 B2 | 4/2006 | Szuba |
| 7,037,272 B2 | 5/2006 | Silpachai et al. |
| 7,111,344 B2 | 9/2006 | French |
| 7,264,586 B2 | 9/2007 | Mackin et al. |
| 7,364,539 B2 | 4/2008 | Mackin et al. |
| 7,810,181 B2 | 10/2010 | Brewin et al. |
| 7,886,384 B2 | 2/2011 | Lord |
| 8,001,630 B2 | 8/2011 | Burkholder et al. |
| 8,291,530 B2 | 12/2012 | Burkholder et al. |
| 8,864,665 B2 | 10/2014 | Rotondo et al. |
| 8,893,325 B2 | 11/2014 | Arnold, IV et al. |
| 8,943,615 B2 | 2/2015 | Howard et al. |
| 9,364,099 B2 | 6/2016 | Zarate |
| 9,554,958 B2 | 1/2017 | Richards et al. |
| 9,572,528 B1 | 2/2017 | Chang |
| 9,693,589 B2 | 7/2017 | Howard et al. |
| 9,839,302 B2 | 12/2017 | Frost |
| 2006/0116555 A1 | 6/2006 | Pavlidis et al. |
| 2007/0156060 A1 | 7/2007 | Cervantes |
| 2010/0087701 A1 | 4/2010 | Berka et al. |
| 2010/0125949 A1 | 5/2010 | Stebbing |
| 2013/0047336 A1 | 2/2013 | Burkholder et al. |
| 2013/0072767 A1* | 3/2013 | Imamura ................ A61B 5/024 600/301 |
| 2013/0201313 A1 | 8/2013 | Khalil |
| 2013/0342691 A1 | 12/2013 | Lewis et al. |
| 2014/0091945 A1* | 4/2014 | Rivas ................... A61B 5/113 340/870.01 |
| 2014/0140368 A1 | 5/2014 | Yildizyan et al. |
| 2014/0296661 A1 | 10/2014 | Zwartkruis-pelgrim et al. |
| 2015/0105608 A1 | 4/2015 | Lipoma et al. |
| 2015/0195494 A1 | 7/2015 | Alvarez |
| 2015/0288877 A1* | 10/2015 | Glazer ................. H04N 5/2251 348/77 |
| 2016/0035205 A1* | 2/2016 | Messenger ............ A61B 5/746 340/539.15 |
| 2016/0210747 A1 | 7/2016 | Hay et al. |
| 2016/0217588 A1 | 7/2016 | Hay |
| 2016/0287075 A1 | 10/2016 | Pradeep et al. |
| 2016/0310046 A1 | 10/2016 | Heinrich et al. |
| 2016/0310067 A1 | 10/2016 | Heinrich et al. |
| 2016/0345832 A1 | 12/2016 | Pavagada Nagaraja et al. |
| 2016/0364617 A1 | 12/2016 | Silberschatz et al. |
| 2017/0108236 A1 | 4/2017 | Guan et al. |
| 2017/0258398 A1 | 9/2017 | Jackson |
| 2017/0374296 A1 | 12/2017 | Schmidt |
| 2018/0064369 A1* | 3/2018 | Gunther ................ A61B 5/4806 |
| 2018/0330169 A1 | 11/2018 | Van Hoof et al. |

OTHER PUBLICATIONS

Non-Final Office Action dated Aug. 13, 2019 in U.S. Appl. No. 15/859,650, all pages.
Final Office action dated Jul. 12, 2019 in U.S. Appl. No. 15/859,654, all pages.

* cited by examiner

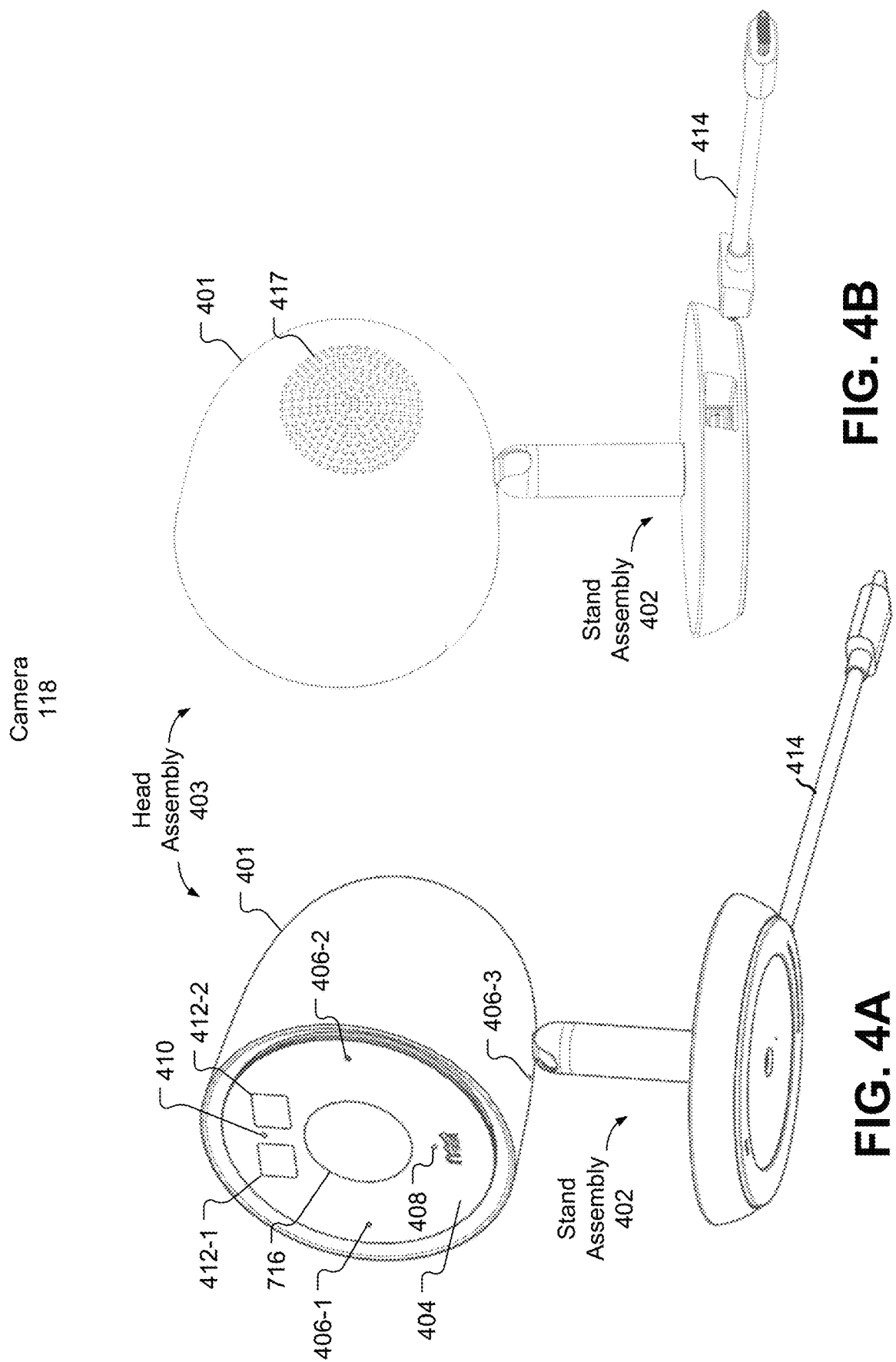

ENHANCED VISUALIZATION OF BREATHING OR HEARTBEAT OF AN INFANT OR OTHER MONITORED SUBJECT

CROSS REFERENCE TO RELATED APPLICATIONS

This patent application is related to U.S. patent application Ser. No. 15/859,650, entitled "INFANT MONITORING SYSTEM WITH VIDEO-BASED TEMPERATURE BASELINING AND ELEVATED TEMPERATURE DETECTION" filed Dec. 31, 2017, which is hereby incorporated by reference in its entirety for all purposes.

This patent application is also related to U.S. patent application Ser. No. 15/859,654, entitled "INFANT MONITORING SYSTEM WITH OBSERVATION-BASED SYSTEM CONTROL AND FEEDBACK LOOPS" filed Dec. 31, 2017, which is hereby incorporated by reference in its entirety for all purposes.

TECHNICAL FIELD

This patent specification relates generally to a smart-home environment for monitoring subject. More particularly, this patent specification describes automatic control of smart-home devices, such as video camera assemblies, keypads, security system sensors, thermostats, hazard detectors, doorbells, and/or the like, to create and/or monitor an optimal sleep environment for a monitored subject.

BACKGROUND

Smart-home devices are rapidly becoming part of the modern home experience. These devices may include thermostats, keypads, touch screens, and/or other control devices for controlling environmental systems, such as HVAC systems or lighting systems. The smart-home environment may also include smart appliances, such as washing machines, dishwashers, refrigerators, garbage cans, and so forth, that interface with control and/or monitoring devices to increase the level of functionality and control provided to an occupant. Security systems, including cameras, keypads, sensors, motion detectors, glass-break sensors, microphones, and so forth, may also be installed as part of the smart-home architecture. Other smart-the home devices may include doorbells, monitoring systems, hazard detectors, smart lightbulbs, and virtually any other electronic device that can be controlled via a wired/wireless network.

Many modern smart-home environments may include video cameras. These video cameras may be used for security systems, monitoring systems, hazard detection systems, and so forth. In general, video cameras provide a live video feed that can be played at a local console or on a computing system of the user, allowing them to remotely monitor a portion of the smart-home environment or its surroundings.

BRIEF SUMMARY

In some embodiments, a method of monitoring physical characteristics of subjects in sleep environments may include receiving, through a video camera, a video feed of a subject in a sleep environment. The method may also include analyzing the video feed of the subject to identify motion of the subject in the video feed. The method may additionally include causing a mobile device to present a representation of the motion of the subject, wherein the motion of the subject is exaggerated.

In some embodiments, a system for monitoring physical characteristics of subjects in sleep environments may include a video camera, one or more processors, and one or more memory devices comprising instructions that, when executed by the one or more processors, cause the one or more processors to perform operations that may include receiving, through a video camera, a video feed of a subject in a sleep environment. The operations may also include analyzing the video feed of the subject to identify motion of the subject in the video feed. The operations may additionally include causing a mobile device to present a representation of the motion of the subject, wherein the motion of the subject is exaggerated.

A further understanding of the nature and advantages of the present invention may be realized by reference to the remaining portions of the specification and the drawings. Also note that other embodiments may be described in the following disclosure and claims.

BRIEF DESCRIPTION OF THE DRAWINGS

FIG. 4A illustrates a view of a representative camera assembly in accordance with some implementations.

FIG. 4B illustrates a view of a representative camera assembly in accordance with some implementations.

DETAILED DESCRIPTION

In the following detailed description, for purposes of explanation, numerous specific details are set forth to provide a thorough understanding of the various embodiments of the present invention. Those of ordinary skill in the art will realize that these various embodiments of the present invention are illustrative only and are not intended to be limiting in any way. Other embodiments of the present invention will readily suggest themselves to such skilled persons having the benefit of this disclosure. It will be apparent to one skilled in the art that the present invention may be practiced without some or all of these specific details. In other instances, well known details have not been described in detail in order not to unnecessarily obscure the present invention.

In addition, for clarity purposes, not all of the routine features of the embodiments described herein are shown or described. One of ordinary skill in the art would readily appreciate that in the development of any such actual embodiment, numerous embodiment-specific decisions may be required to achieve specific design objectives. These design objectives will vary from one embodiment to another and from one developer to another. Moreover, it will be appreciated that such a development effort might be complex and time-consuming but would nevertheless be a routine engineering undertaking for those of ordinary skill in the art having the benefit of this disclosure.

Figure 1:
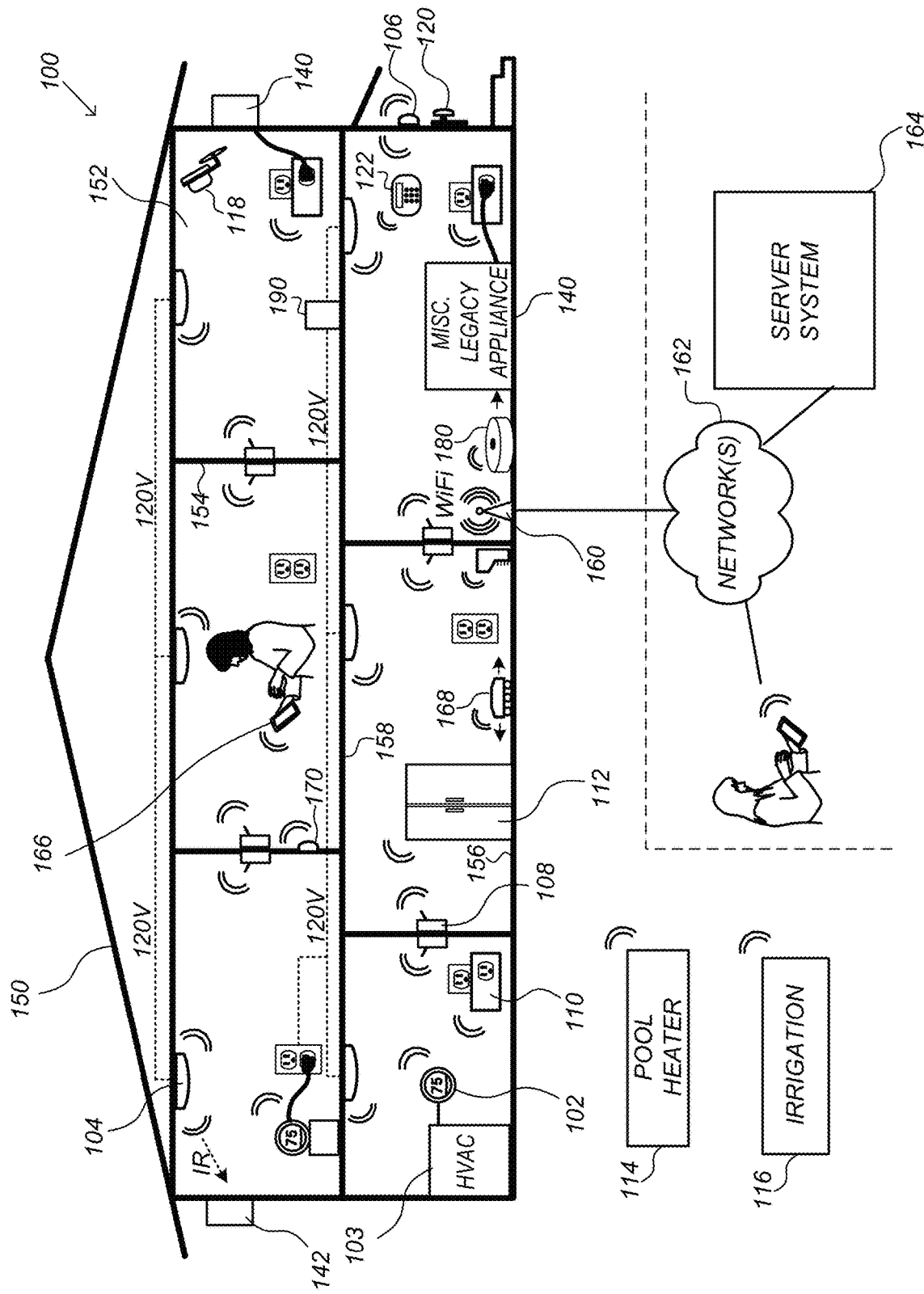
FIG. 1 is an example of a smart-home environment within which one or more of the devices, methods, systems, services, and/or computer program products described further herein will be applicable, according to some embodiments.

FIG. 1 illustrates an example smart-home environment 100, according to some embodiments. The smart-home environment 100 includes a structure 150 (e.g., a house, office building, garage, or mobile home) with various integrated devices. It will be appreciated that devices may also be integrated into a smart-home environment 100 that does not include an entire structure 150, such as an apartment, condominium, or office space. Further, the smart-home environment 100 may control and/or be coupled to devices outside of the actual structure 150. Indeed, several devices in the smart-home environment 100 need not be physically within the structure 150. For example, a device controlling a pool heater 114 or irrigation system 116 may be located outside of the structure 150.

The term "smart-home environment" may refer to smart environments for homes such as a single-family house, but the scope of the present teachings is not so limited. The present teachings are also applicable, without limitation, to duplexes, townhomes, multi-unit apartment buildings, hotels, retail stores, office buildings, industrial buildings, and more generally any living space or work space. Similarly, while the terms user, customer, installer, homeowner, occupant, guest, tenant, landlord, repair person, etc., may be used to refer to a person or persons acting in the context of some particular situations described herein, these references do not limit the scope of the present teachings with respect to the person or persons who are performing such actions. Thus, for example, the terms user, customer, purchaser, installer, subscriber, and homeowner may often refer to the same person in the case of a single-family residential dwelling, because the head of the household is often the person who makes the purchasing decision, buys the unit, and installs and configures the unit, as well as being one of the users of the unit. However, in other scenarios, such as a landlord-tenant environment, the customer may be the landlord with respect to purchasing the unit, the installer may be a local apartment supervisor, a first user may be the tenant, and a second user may again be the landlord with respect to remote control functionality. While the identity of the person performing the action may be germane to a particular advantage provided by one or more of the implementations, such an identity should not be construed in the descriptions that follow as necessarily limiting the scope of the present teachings to those particular individuals having those particular identities.

The depicted structure 150 includes a plurality of rooms 152, separated at least partly from each other via walls 154. The walls 154 may include interior walls or exterior walls. Each room may further include a floor 156 and a ceiling 158. Devices may be mounted on, integrated with and/or supported by a wall 154, floor 156, or ceiling 158.

In some implementations, the integrated devices of the smart-home environment 100 include intelligent, multi-sensing, network-connected devices that integrate seamlessly with each other in a smart-home network and/or with a central server or a cloud-computing system to provide a variety of useful smart-home functions. The smart-home environment 100 may include one or more intelligent, multi-sensing, network-connected thermostats 102 (hereinafter referred to as "smart thermostats 102"), one or more intelligent, network-connected, multi-sensing hazard detection units 104 (hereinafter referred to as "smart hazard detectors 104"), one or more intelligent, multi-sensing, network-connected entryway interface devices 106 and 120 (hereinafter referred to as "smart doorbells 106" and "smart door locks 120"), and one or more intelligent, multi-sensing, network-connected alarm systems 122 (hereinafter referred to as "smart alarm systems 122"). Although not depicted explicitly in FIG. 1, the smart-home environment 100 may also include other monitoring systems, such as baby monitoring systems, elderly monitoring systems, handicapped monitoring systems, and so forth.

In some implementations, the one or more smart thermostats 102 detect ambient climate characteristics (e.g., temperature and/or humidity) and control a HVAC system 103 accordingly. For example, a respective smart thermostat 102 includes an ambient temperature sensor.

The one or more smart hazard detectors 104 may include thermal radiation sensors directed at respective heat sources (e.g., a stove, oven, other appliances, a fireplace, etc.). For example, a smart hazard detector 104 in a kitchen 153 may include a thermal radiation sensor directed at a stove/oven 112. A thermal radiation sensor may determine the temperature of the respective heat source (or a portion thereof) at which it is directed and may provide corresponding blackbody radiation data as output.

The smart doorbell 106 and/or the smart door lock 120 may detect a person's approach to or departure from a location (e.g., an outer door), control doorbell/door locking functionality (e.g., receive user inputs from a portable electronic device 166-1 to actuate bolt of the smart door lock 120), announce a person's approach or departure via audio or visual devices, and/or control settings on a security system (e.g., to activate or deactivate the security system when occupants go and come). In some implementations, the smart doorbell 106 may include some or all of the components and features of the camera 118. In some implementations, the smart doorbell 106 includes a camera 118.

The smart alarm system 122 may detect the presence of an individual within close proximity (e.g., using built-in IR sensors), sound an alarm (e.g., through a built-in speaker, or by sending commands to one or more external speakers), and send notifications to entities or users within/outside of the smart-home network 100. In some implementations, the smart alarm system 122 also includes one or more input devices or sensors (e.g., keypad, biometric scanner, NFC transceiver, microphone) for verifying the identity of a user, and one or more output devices (e.g., display, speaker) for providing notifications. In some implementations, the smart alarm system 122 may also be set to an "armed" mode, such that detection of a trigger condition or event causes the alarm to be sounded unless a disarming action is performed.

In some implementations, the smart-home environment 100 may include one or more intelligent, multi-sensing, network-connected wall switches 108 (hereinafter referred to as "smart wall switches 108"), along with one or more intelligent, multi-sensing, network-connected wall plug interfaces 110 (hereinafter referred to as "smart wall plugs 110"). The smart wall switches 108 may detect ambient lighting conditions, detect room-occupancy states, and control a power and/or dim state of one or more lights. In some instances, smart wall switches 108 may also control a power state or speed of a fan, such as a ceiling fan. The smart wall plugs 110 may detect occupancy of a room or enclosure and control supply of power to one or more wall plugs (e.g., such that power is not supplied to the plug if nobody is at home).

In some implementations, the smart-home environment 100 of FIG. 1 may include a plurality of intelligent, multi-sensing, network-connected appliances 112 (hereinafter referred to as "smart appliances 112"), such as refrigerators, stoves, ovens, televisions, washers, dryers, lights, stereos, intercom systems, garage-door openers, floor fans, ceiling fans, wall air conditioners, pool heaters, irrigation systems, security systems, space heaters, window AC units, motorized duct vents, and so forth. In some implementations, when plugged in, an appliance may announce itself to the smart home network, such as by indicating what type of appliance it is, and it may automatically integrate with the controls of the smart home. Such communication by the appliance to the smart home may be facilitated by either a wired or wireless communication protocol. The smart home may also include a variety of non-communicating legacy appliances 140, such as older-model conventional washers/dryers, refrigerators, and/or the like, which may be controlled by smart wall plugs 110. The smart-home environment 100 may further include a variety of partially communicating legacy appliances 142, such as infrared ("IR") controlled wall air conditioners or other IR-controlled devices, which may be controlled by IR signals provided by the smart hazard detectors 104, hand-held remote controls, key FOBs, or the smart wall switches 108.

In some implementations, the smart-home environment 100 may include one or more network-connected cameras 118 that are configured to provide video monitoring and security in the smart-home environment 100. The cameras 118 may be used to determine the occupancy of the structure 150 and/or particular rooms 152 in the structure 150, and thus may act as occupancy sensors. For example, video captured by the cameras 118 may be processed to identify the presence of an occupant in the structure 150 (e.g., in a particular room 152). Specific individuals may be identified based, for example, on their appearance (e.g., height, face) and/or movement (e.g., their walk/gait). Cameras 118 may additionally include one or more sensors (e.g., IR sensors, motion detectors), input devices (e.g., microphone for capturing audio), and output devices (e.g., speaker for outputting audio). In some implementations, the cameras 118 may each be configured to operate in a day mode and in a low-light mode (e.g., a night mode). In some implementations, the cameras 118 each include one or more IR illuminators for providing illumination while the camera is operating in the low-light mode. In some implementations, the cameras 118 include one or more outdoor cameras. In some implementations, the outdoor cameras include additional features and/or components such as weatherproofing and/or solar ray compensation.

The smart-home environment 100 may additionally or alternatively include one or more other occupancy sensors (e.g., the smart doorbell 106, smart door locks 120, touch screens, IR sensors, microphones, ambient light sensors, motion detectors, smart nightlights 170, etc.). In some implementations, the smart-home environment 100 may include radio-frequency identification (RFID) readers (e.g., in each room 152 or a portion thereof) that determine occupancy based on RFID tags located on or embedded in occupants. For example, RFID readers may be integrated into the smart hazard detectors 104, and RFID tags may be worn in users clothing for integrated in hand-held devices such as a smart phone.

The smart-home environment 100 may also include communication with devices outside of the physical home but within a proximate geographical range of the home. For example, the smart-home environment 100 may include a pool heater monitor 114 that communicates a current pool temperature to other devices within the smart-home environment 100 and/or receives commands for controlling the pool temperature. Similarly, the smart-home environment 100 may include an irrigation monitor 116 that communicates information regarding irrigation systems within the smart-home environment 100 and/or receives control information for controlling such irrigation systems.

By virtue of network connectivity, one or more of the smart home devices of FIG. 1 may further allow a user to interact with the device even if the user is not proximate to the device. For example, a user may communicate with a device using a computer (e.g., a desktop computer, laptop computer, or tablet) or other portable electronic device 166 (e.g., a mobile phone, such as a smart phone). A webpage or application may be configured to receive communications from the user and control the device based on the communications and/or to present information about the device's operation to the user. For example, the user may view a current set point temperature for a device (e.g., a stove) and adjust it using a computer. The user may be in the structure during this remote communication or outside the structure.

As discussed above, users may control smart devices in the smart-home environment 100 using a network-connected computer or portable electronic device 166. In some examples, some or all of the occupants (e.g., individuals who live in the home) may register their device 166 with the smart-home environment 100. Such registration may be made at a central server to authenticate the occupant and/or the device as being associated with the home and to give permission to the occupant to use the device to control the smart devices in the home. An occupant may use their registered device 166 to remotely control the smart devices of the home, such as when the occupant is at work or on vacation. The occupant may also use their registered device to control the smart devices when the occupant is actually located inside the home, such as when the occupant is sitting on a couch inside the home. It should be appreciated that instead of or in addition to registering devices 166, the smart-home environment 100 may make inferences about (1) which individuals live in the home and are therefore occupants, and (2) which devices 166 are associated with those individuals. As such, the smart-home environment may "learn" who is an occupant and permit the devices 166 associated with those individuals to control the smart devices of the home.

In some implementations, in addition to containing processing and sensing capabilities, devices 102, 104, 106, 108, 110, 112, 114, 116, 118, 120, and/or 122 (collectively referred to as "the smart devices" or "the smart-home devices") are capable of data communications and information sharing with other smart devices, a central server or cloud-computing system, and/or other devices that are network-connected. Data communications may be carried out using any of a variety of custom or standard wireless protocols (e.g., IEEE 802.15.4, Wi-Fi, ZigBee, 6LoWPAN, Thread, Z-Wave, Bluetooth Smart, ISA100.5A, WirelessHART, MiWi, etc.) and/or any of a variety of custom or standard wired protocols (e.g., Ethernet, HomePlug, etc.), or any other suitable communication protocol, including communication protocols not yet developed as of the filing date of this document.

In some implementations, the smart devices may serve as wireless or wired repeaters. In some implementations, a first one of the smart devices communicates with a second one of the smart devices via a wireless router. The smart devices may further communicate with each other via a connection (e.g., network interface 160) to a network, such as the Internet 162. Through the Internet 162, the smart devices may communicate with a server system 164 (also called a central server system and/or a cloud-computing system herein). The server system 164 may be associated with a manufacturer, support entity, or service provider associated with the smart device(s). In some implementations, a user is able to contact customer support using a smart device itself rather than needing to use other communication means, such as a telephone or Internet-connected computer. In some implementations, software updates are automatically sent from the server system 164 to smart devices (e.g., when available, when purchased, or at routine intervals).

In some implementations, the network interface 160 includes a conventional network device (e.g., a router), and the smart-home environment 100 of FIG. 1 includes a hub device 180 that is communicatively coupled to the network(s) 162 directly or via the network interface 160. The hub device 180 may be further communicatively coupled to one or more of the above intelligent, multi-sensing, network-connected devices (e.g., smart devices of the smart-home environment 100). Each of these smart devices optionally communicates with the hub device 180 using one or more radio communication networks available at least in the smart-home environment 100 (e.g., ZigBee, Z-Wave, Insteon, Bluetooth, Wi-Fi and other radio communication networks). In some implementations, the hub device 180 and devices coupled with/to the hub device can be controlled and/or interacted with via an application running on a smart phone, household controller, laptop, tablet computer, game console or similar electronic device. In some implementations, a user of such controller application can view status of the hub device or coupled smart devices, configure the hub device to interoperate with smart devices newly introduced to the home network, commission new smart devices, and adjust or view settings of connected smart devices, etc. In some implementations the hub device extends the capabilities of low-capability smart devices to match the capabilities of the highly capable smart devices of the same type, integrates functionality of multiple different device types—even across different communication protocols, and is configured to streamline adding of new devices and commissioning of the hub device. In some implementations, hub device 180 further comprises a local storage device for storing data related to, or output by, smart devices of smart-home environment 100. In some implementations, the data includes one or more of: video data output by a camera device, metadata output by a smart device, settings information for a smart device, usage logs for a smart device, and the like.

In some implementations, smart-home environment 100 includes a local storage device 190 for storing data related to, or output by, smart devices of smart-home environment 100. In some implementations, the data includes one or more of: video data output by a camera device (e.g., camera 118), metadata output by a smart device, settings information for a smart device, usage logs for a smart device, and the like. In some implementations, local storage device 190 is communicatively coupled to one or more smart devices via a smart home network. In some implementations, local storage device 190 is selectively coupled to one or more smart devices via a wired and/or wireless communication network. In some implementations, local storage device 190 is used to store video data when external network conditions are poor. For example, local storage device 190 is used when an encoding bitrate of camera 118 exceeds the available bandwidth of the external network (e.g., network(s) 162). In some implementations, local storage device 190 temporarily stores video data from one or more cameras (e.g., camera 118) prior to transferring the video data to a server system (e.g., server system 164).

In some implementations, the smart-home environment 100 includes service robots 168 that are configured to carry out, in an autonomous manner, any of a variety of household tasks.

Figure 2A:
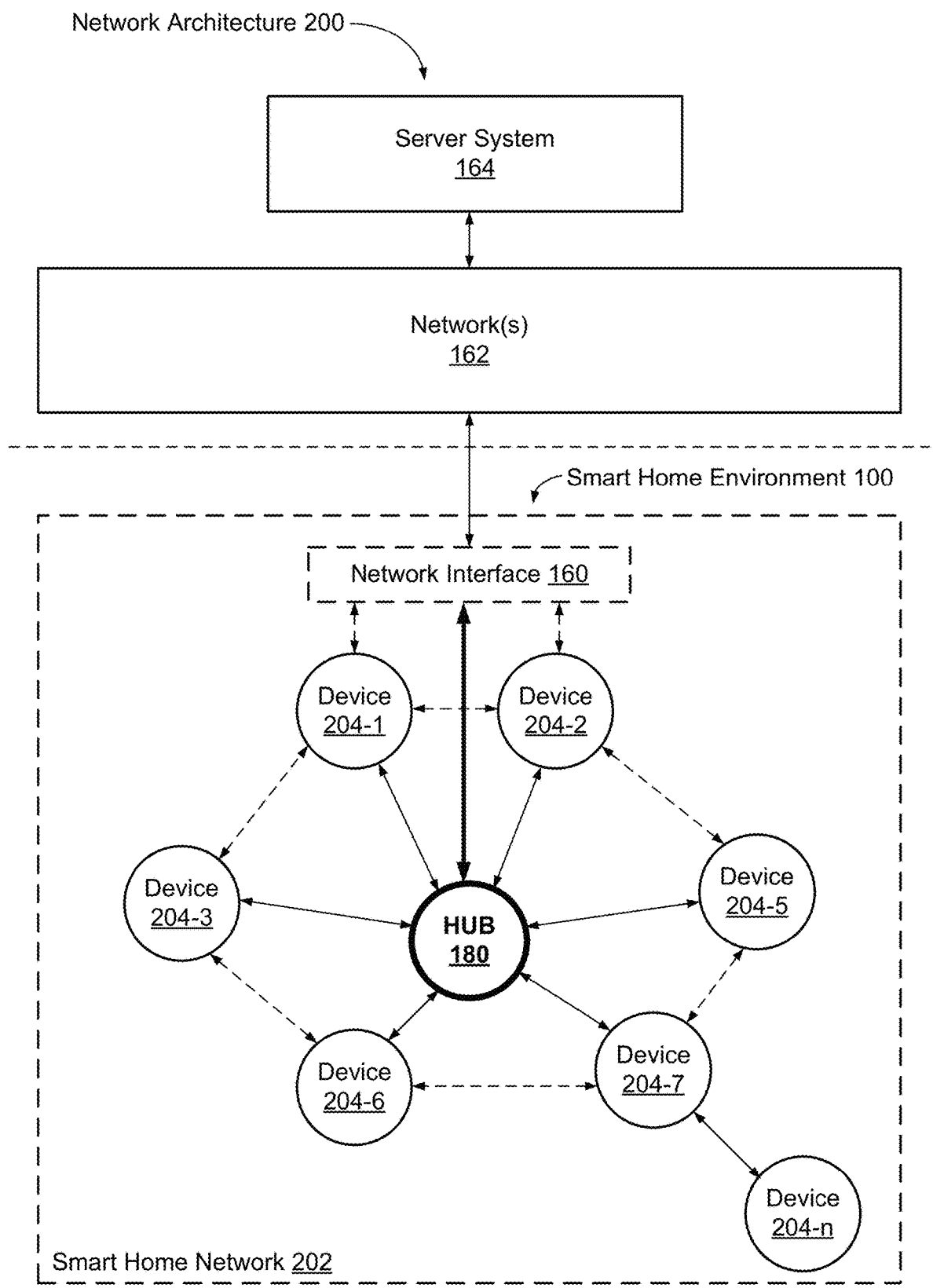
FIG. 2A illustrates a simplified block diagram of a representative network architecture that includes a smart-home network in accordance, according to some embodiments.

FIG. 2A illustrates a simplified block diagram of a representative network architecture 200 that includes a smart home network 202 in accordance with some implementations. In some implementations, the smart devices 204 in the smart-home environment 100 (e.g., devices 102, 104, 106, 108, 110, 112, 114, 116, 118, 120, and/or 122) combine with the hub device 180 to create a mesh network in smart home network 202. In some implementations, one or more smart devices 204 in the smart home network 202 operate as a smart home controller. Additionally and/or alternatively, hub device 180 operates as the smart home controller. In some implementations, a smart home controller has more computing power than other smart devices. In some implementations, a smart home controller processes inputs (e.g., from smart devices 204, electronic device 166, and/or server system 164) and sends commands (e.g., to smart devices 204 in the smart home network 202) to control operation of the smart-home environment 100. In some implementations, some of the smart devices 204 in the smart home network 202 (e.g., in the mesh network) are "spokesman" nodes (e.g., 204-1) and others are "low-powered" nodes (e.g., 204-9). Some of the smart devices in the smart-home environment 100 are battery powered, while others have a regular and reliable power source, such as by connecting to wiring (e.g., to 120V line voltage wires) behind the walls 154 of the smart-home environment. The smart devices that have a regular and reliable power source are referred to as "spokesman" nodes. These nodes are typically equipped with the capability of using a wireless protocol to facilitate bidirectional communication with a variety of other devices in the smart-home environment 100, as well as with the server system 164. In some implementations, one or more "spokesman" nodes operate as a smart home controller. On the other hand, the devices that are battery powered are the "low-power" nodes. These nodes tend to be smaller than spokesman nodes and typically only communicate using wireless protocols that require very little power, such as Zigbee, ZWave, 6LoWPAN, Thread, Bluetooth, etc.

In some implementations, some low-power nodes may be incapable of bidirectional communication. These low-power nodes may send messages, but they are unable to "listen." Thus, other devices in the smart-home environment 100, such as the spokesman nodes, need not send information to these low-power nodes. In some implementations, some low-power nodes are capable of only a limited bidirectional communication. For example, other devices are able to communicate with the low-power nodes only during a certain time period.

In some implementations, the smart devices may serve as low-power and spokesman nodes to create a mesh network in the smart-home environment 100. In some implementations, individual low-power nodes in the smart-home environment may regularly send out messages regarding what they are sensing, and the other low-powered nodes in the smart-home environment—in addition to sending out their own messages—may forward these messages, thereby causing the messages to travel from node to node (i.e., device to device) throughout the smart home network 202. In some implementations, the spokesman nodes in the smart home network 202, which are able to communicate using a relatively high-power communication protocol, such as IEEE 802.11, are able to switch to a relatively low-power communication protocol, such as IEEE 802.15.4, to receive these messages, translate the messages to other communication protocols, and send the translated messages to other spokesman nodes and/or the server system 164 (using, e.g., the relatively high-power communication protocol). Thus, the low-powered nodes using low-power communication protocols are able to send and/or receive messages across the entire smart home network 202, as well as over the Internet 162 to the server system 164. In some implementations, the mesh network enables the server system 164 to regularly receive data from most or all of the smart devices in the home, make inferences based on the data, facilitate state synchronization across devices within and outside of the smart home network 202, and send commands to one or more of the smart devices to perform tasks in the smart-home environment.

The spokesman nodes and some of the low-powered nodes are capable of "listening." Accordingly, users, other devices, and/or the server system 164 may communicate control commands to the low-powered nodes. For example, a user may use the electronic device 166 (e.g., a smart phone) to send commands over the Internet to the server system 164, which then relays the commands to one or more spokesman nodes in the smart home network 202. The spokesman nodes may use a low-power protocol to communicate the commands to the low-power nodes throughout the smart home network 202, as well as to other spokesman nodes that did not receive the commands directly from the server system 164.

In some implementations, a smart nightlight 170, which is an example of a smart device 204, is a low-power node. In addition to housing a light source, the smart nightlight 170 houses an occupancy sensor, such as an ultrasonic or passive IR sensor, and an ambient light sensor, such as a photo resistor or a single-pixel sensor that measures light in the room. In some implementations, the smart nightlight 170 is configured to activate the light source when its ambient light sensor detects that the room is dark and when its occupancy sensor detects that someone is in the room. In other implementations, the smart nightlight 170 is simply configured to activate the light source when its ambient light sensor detects that the room is dark. Further, in some implementations, the smart nightlight 170 includes a low-power wireless communication chip (e.g., a ZigBee chip) that regularly sends out messages regarding the occupancy of the room and the amount of light in the room, including instantaneous messages coincident with the occupancy sensor detecting the presence of a person in the room. As described above, these messages may be sent wirelessly (e.g., using the mesh network) from node to node (i.e., smart device to smart device) within the smart home network 202 as well as over the Internet 162 to the server system 164.

Other examples of low-power nodes include battery-operated versions of the smart hazard detectors 104. These smart hazard detectors 104 are often located in an area without access to constant and reliable power and may include any number and type of sensors, such as smoke/fire/heat sensors (e.g., thermal radiation sensors), carbon monoxide/dioxide sensors, occupancy/motion sensors, ambient light sensors, ambient temperature sensors, humidity sensors, and the like. Furthermore, smart hazard detectors 104 may send messages that correspond to each of the respective sensors to the other devices and/or the server system 164, such as by using the mesh network as described above.

Examples of spokesman nodes include smart doorbells 106, smart thermostats 102, smart wall switches 108, and smart wall plugs 110. These devices are often located near and connected to a reliable power source, and therefore may include more power-consuming components, such as one or more communication chips capable of bidirectional communication in a variety of protocols.

As explained above with reference to FIG. 1, in some implementations, the smart-home environment 100 of FIG. 1 includes a hub device 180 that is communicatively coupled to the network(s) 162 directly or via the network interface 160. The hub device 180 is further communicatively coupled to one or more of the smart devices using a radio communication network that is available at least in the smart-home environment 100. Communication protocols used by the radio communication network include, but are not limited to, ZigBee, Z-Wave, Insteon, EuOcean, Thread, OSIAN, Bluetooth Low Energy and the like. In some implementations, the hub device 180 not only converts the data received from each smart device to meet the data format requirements of the network interface 160 or the network(s) 162, but also converts information received from the network interface 160 or the network(s) 162 to meet the data format requirements of the respective communication protocol associated with a targeted smart device. In some implementations, in addition to data format conversion, the hub device 180 further processes the data received from the smart devices or information received from the network interface 160 or the network(s) 162 preliminary. For example, the hub device 180 can integrate inputs from multiple sensors/connected devices (including sensors/devices of the same and/or different types), perform higher level processing on those inputs—e.g., to assess the overall environment and coordinate operation among the different sensors/devices—and/or provide instructions to the different devices based on the collection of inputs and programmed processing. It is also noted that in some implementations, the network interface 160 and the hub device 180 are integrated to one network device. Functionality described herein is representative of particular implementations of smart devices, control application(s) running on representative electronic device(s) (such as a smart phone), hub device(s) 180, and server(s) coupled to hub device(s) via the Internet or other Wide Area Network (WAN). All or a portion of this functionality and associated operations can be performed by any elements of the described system—for example, all or a portion of the functionality described herein as being performed by an implementation of the hub device can be performed, in different system implementations, in whole or in part on the server, one or more connected smart devices and/or the control application, or different combinations thereof.

Figure 2B:
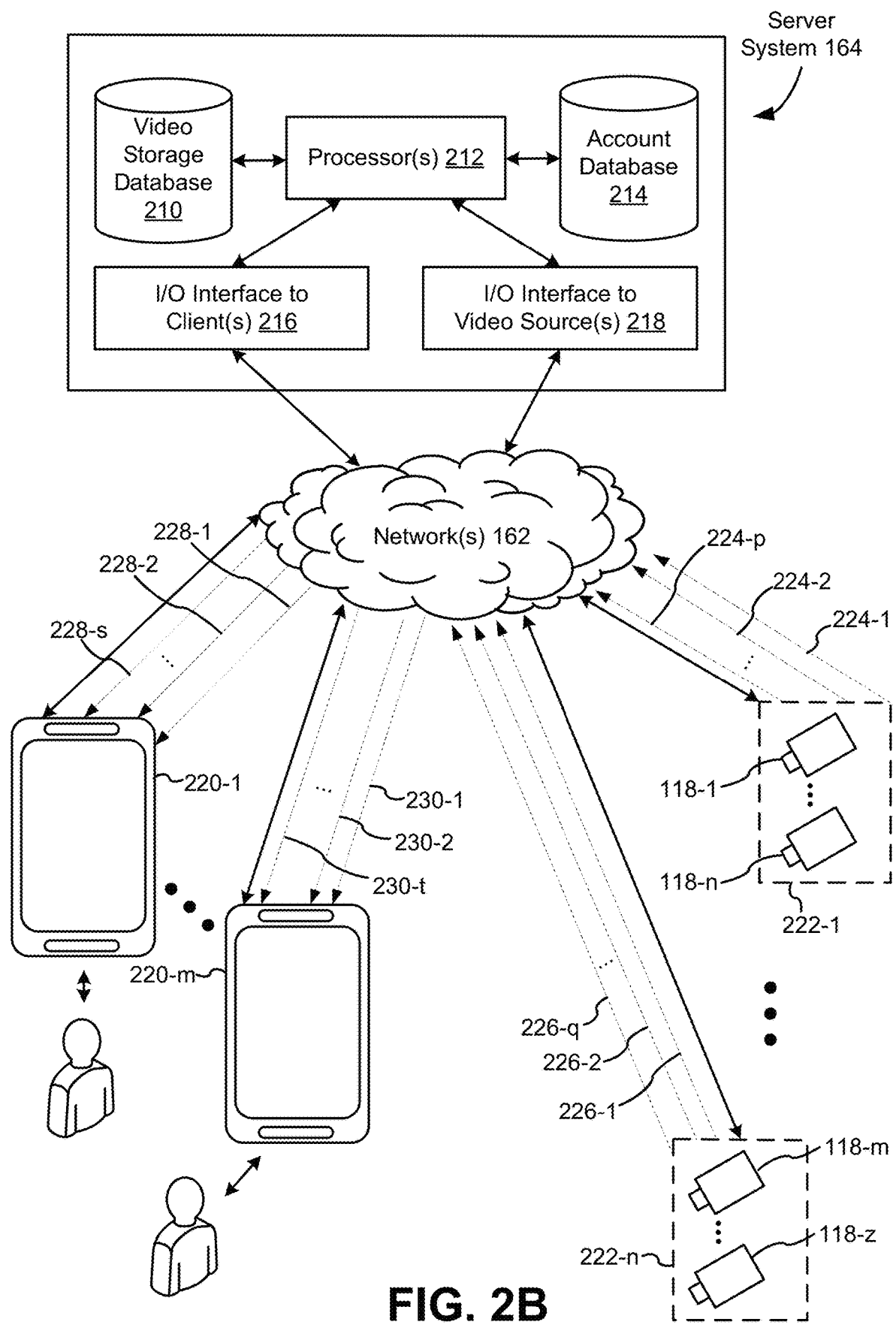
FIG. 2B illustrates a simplified operating environment in which a server system interacts with client devices and smart devices, according to some embodiments.

FIG. 2B illustrates a representative operating environment in which a server system 164 provides data processing for monitoring and facilitating review of events (e.g., motion, audio, security, etc.) in video streams captured by video cameras 118. As shown in FIG. 2B, the server system 164 receives video data from video sources 222 (including cameras 118) located at various physical locations (e.g., inside homes, restaurants, stores, streets, parking lots, and/or the smart-home environments 100 of FIG. 1). Each video source 222 may be bound to one or more reviewer accounts, and the server system 164 provides video monitoring data for the video source 222 to client devices 220 associated with the reviewer accounts. For example, the portable electronic device 166 is an example of the client device 220. In some implementations, the server system 164 is a video processing server that provides video processing services to video sources and client devices 220.

In some implementations, each of the video sources 222 includes one or more video cameras 118 that capture video and send the captured video to the server system 164 substantially in real-time. In some implementations, each of the video sources 222 includes a controller device (not shown) that serves as an intermediary between the one or more cameras 118 and the server system 164. The controller device receives the video data from the one or more cameras 118, optionally performs some preliminary processing on the video data, and sends the video data to the server system 164 on behalf of the one or more cameras 118 substantially in real-time. In some implementations, each camera has its own on-board processing capabilities to perform some preliminary processing on the captured video data before sending the processed video data (along with metadata obtained through the preliminary processing) to the controller device and/or the server system 164.

In accordance with some implementations, each of the client devices 220 includes a client-side module. The client-side module communicates with a server-side module executed on the server system 164 through the one or more networks 162. The client-side module provides client-side functionality for the event monitoring and review processing and communications with the server-side module. The server-side module provides server-side functionality for event monitoring and review processing for any number of client-side modules each residing on a respective client device 220. The server-side module also provides server-side functionality for video processing and camera control for any number of the video sources 222, including any number of control devices and the cameras 118.

In some implementations, the server system 164 includes one or more processors 212, a video storage database 210, an account database 214, an I/O interface to one or more client devices 216, and an I/O interface to one or more video sources 218. The I/O interface to one or more clients 216 facilitates the client-facing input and output processing. The account database 214 stores a plurality of profiles for reviewer accounts registered with the video processing server, where a respective user profile includes account credentials for a respective reviewer account, and one or more video sources linked to the respective reviewer account. The I/O interface to one or more video sources 218 facilitates communications with one or more video sources 222 (e.g., groups of one or more cameras 118 and associated controller devices). The video storage database 210 stores raw video data received from the video sources 222, as well as various types of metadata, such as motion events, event categories, event category models, event filters, and event masks, for use in data processing for event monitoring and review for each reviewer account.

Examples of a representative client device 220 include a handheld computer, a wearable computing device, a personal digital assistant (PDA), a tablet computer, a laptop computer, a desktop computer, a cellular telephone, a smart phone, an enhanced general packet radio service (EGPRS) mobile phone, a media player, a navigation device, a game console, a television, a remote control, a point-of-sale (POS) terminal, a vehicle-mounted computer, an eBook reader, or a combination of any two or more of these data processing devices or other data processing devices.

Examples of the one or more networks 162 include local area networks (LAN) and wide area networks (WAN) such as the Internet. The one or more networks 162 are implemented using any known network protocol, including various wired or wireless protocols, such as Ethernet, Universal Serial Bus (USB), FIREWIRE, Long Term Evolution (LTE), Global System for Mobile Communications (GSM), Enhanced Data GSM Environment (EDGE), code division multiple access (CDMA), time division multiple access (TDMA), Bluetooth, Wi-Fi, voice over Internet Protocol (VoIP), Wi-MAX, or any other suitable communication protocol.

In some implementations, the server system 164 may be implemented on one or more standalone data processing apparatuses or a distributed network of computers. In some implementations, the server system 164 also employs various virtual devices and/or services of third party service providers (e.g., third-party cloud service providers) to provide the underlying computing resources and/or infrastructure resources of the server system 164. In some implementations, the server system 164 includes, but is not limited to, a server computer, a handheld computer, a tablet computer, a laptop computer, a desktop computer, or a combination of any two or more of these data processing devices or other data processing devices.

The server-client environment shown in FIG. 2B includes both a client-side portion (e.g., the client-side module) and a server-side portion (e.g., the server-side module). The division of functionality between the client and server portions of operating environment can vary in different implementations. Similarly, the division of functionality between a video source 222 and the server system 164 can vary in different implementations. For example, in some implementations, the client-side module is a thin-client that provides only user-facing input and output processing functions, and delegates all other data processing functionality to a backend server (e.g., the server system 164). Similarly, in some implementations, a respective one of the video sources 222 is a simple video capturing device that continuously captures and streams video data to the server system 164 with limited or no local preliminary processing on the video data. Although many aspects of the present technology are described from the perspective of the server system 164, the corresponding actions performed by a client device 220 and/or the video sources 222 would be apparent to one of skill in the art. Similarly, some aspects of the present technology may be described from the perspective of a client device or a video source, and the corresponding actions performed by the video server would be apparent to one of skill in the art. Furthermore, some aspects of the present technology may be performed by the server system 164, a client device 220, and a video source 222 cooperatively.

In some implementations, a video source 222 (e.g., a camera 118) transmits one or more streams of video data to the server system 164. In some implementations, the one or more streams may include multiple streams, of respective resolutions and/or frame rates, of the raw video captured by the camera 118. In some implementations, the multiple streams may include a "primary" stream with a certain resolution and frame rate, corresponding to the raw video captured by the camera 118, and one or more additional streams. An additional stream may be the same video stream as the "primary" stream but at a different resolution and/or frame rate, or a stream that captures a portion of the "primary" stream (e.g., cropped to include a portion of the field of view or pixels of the primary stream) at the same or different resolution and/or frame rate as the "primary" stream.

In some implementations, one or more of the streams are sent from the video source 222 directly to a client device 220 (e.g., without being routed to, or processed by, the server system 164). In some implementations, one or more of the streams is stored at the camera 118 (e.g., in memory 406, FIG. 4) and/or a local storage device (e.g., a dedicated recording device), such as a digital video recorder (DVR). For example, in accordance with some implementations, the camera 118 stores the most recent 24 hours of video footage recorded by the camera. In some implementations, portions of the one or more streams are stored at the camera 118 and/or the local storage device (e.g., portions corresponding to particular events or times of interest).

In some implementations, the server system 164 transmits one or more streams of video data to a client device 220 to facilitate event monitoring by a user. In some implementations, the one or more streams may include multiple streams, of respective resolutions and/or frame rates, of the same video feed. In some implementations, the multiple streams may include a "primary" stream with a certain resolution and frame rate, corresponding to the video feed, and one or more additional streams. An additional stream may be the same video stream as the "primary" stream but at a different resolution and/or frame rate, or a stream that shows a portion of the "primary" stream (e.g., cropped to include portion of the field of view or pixels of the primary stream) at the same or different resolution and/or frame rate as the "primary" stream, as described in greater detail in U.S. patent application Ser. No. 15/594,518, which is incorporated herein by reference.

Figure 3:
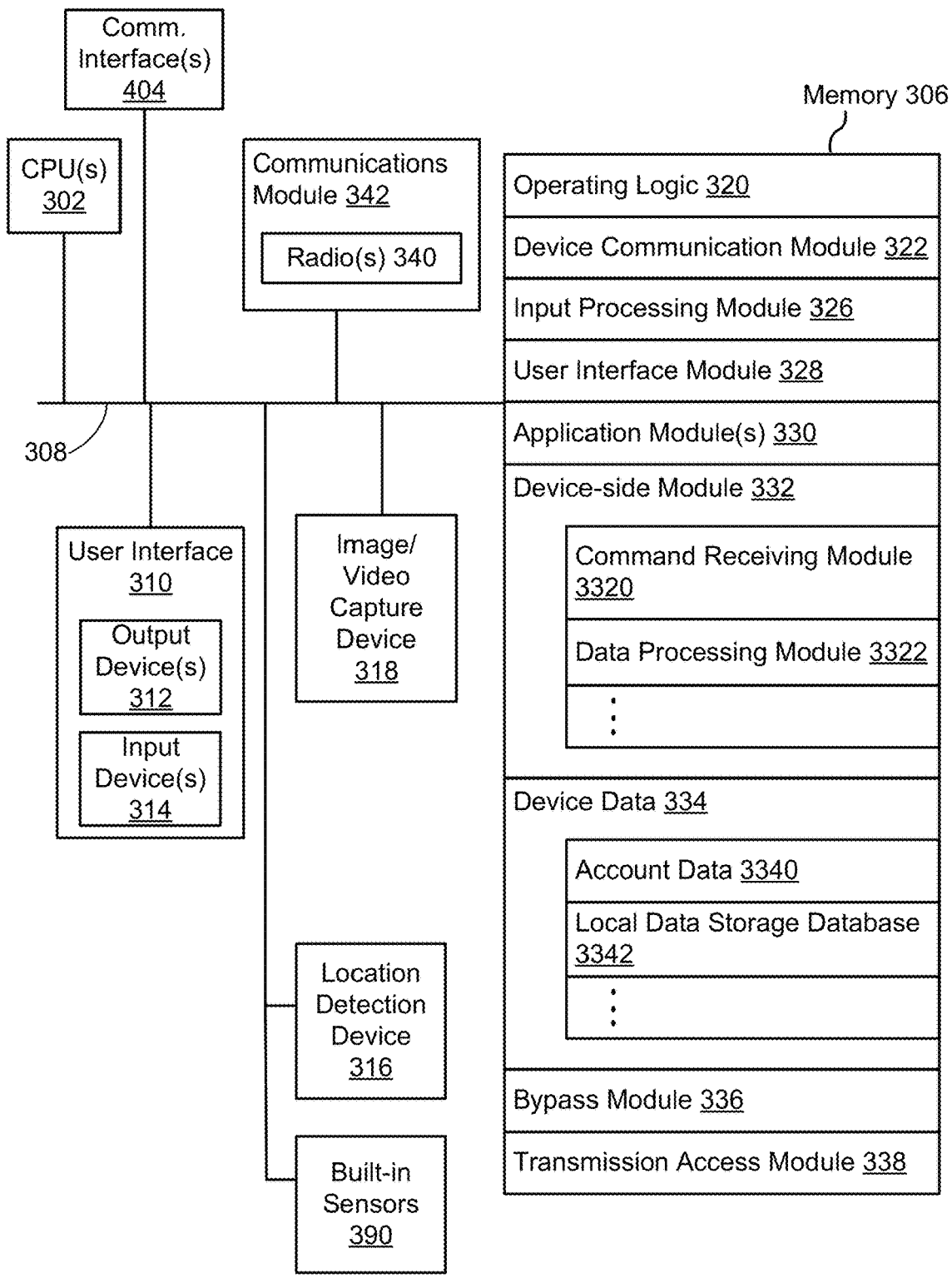
FIG. 3 illustrates a block diagram of a representative smart device in accordance with some implementations.

FIG. 3 illustrates a block diagram of a representative smart device 204 in accordance with some implementations. In some implementations, the smart device 204 (e.g., any devices of a smart-home environment 100, FIG. 1) includes one or more processing units (e.g., CPUs, ASICs, FPGAs, microprocessors, and the like) 302, one or more communication interfaces 304, memory 306, communications module 342 with radios 340, and one or more communication buses 308 for interconnecting these components (sometimes called a chipset). In some implementations, the user interface 310 includes one or more output devices 312 that enable presentation of media content, including one or more speakers and/or one or more visual displays. In some implementations, the user interface 310 also includes one or more input devices 314, including user interface components that facilitate user input such as a keyboard, a mouse, a voice-command input unit or microphone, a touch screen display, a touch-sensitive input pad, a gesture capturing camera, or other input buttons or controls. Furthermore, some smart devices 204 use a microphone and voice recognition or a camera and gesture recognition to supplement or replace the keyboard. In some implementations, the smart device 204 includes one or more image/video capture devices 318 (e.g., cameras, video cameras, scanners, photo sensor units). The built-in sensors 390 may include, for example, one or more thermal radiation sensors, ambient temperature sensors, humidity sensors, IR sensors, occupancy sensors (e.g., using RFID sensors), ambient light sensors, motion detectors, accelerometers, and/or gyroscopes.

The radios 340 enable one or more radio communication networks in the smart-home environments, and allow a smart device 204 to communicate with other devices. In some implementations, the radios 340 are capable of data communications using any of a variety of custom or standard wireless protocols (e.g., IEEE 802.15.4, Wi-Fi, ZigBee, 6LoWPAN, Thread, Z-Wave, Bluetooth Smart, ISA100.5A, WirelessHART, MiWi, etc.) custom or standard wired protocols (e.g., Ethernet, HomePlug, etc.), and/or any other suitable communication protocol, including communication protocols not yet developed as of the filing date of this document.

The communication interfaces 304 include, for example, hardware capable of data communications using any of a variety of custom or standard wireless protocols (e.g., IEEE 802.15.4, Wi-Fi, ZigBee, 6LoWPAN, Thread, Z-Wave, Bluetooth Smart, ISA100.5A, WirelessHART, MiWi, etc.) and/or any of a variety of custom or standard wired protocols (e.g., Ethernet, HomePlug, etc.), or any other suitable communication protocol, including communication protocols not yet developed as of the filing date of this document.

The memory 306 includes high-speed random access memory, such as DRAM, SRAM, DDR RAM, or other random access solid state memory devices; and, optionally, includes non-volatile memory, such as one or more magnetic disk storage devices, one or more optical disk storage devices, one or more flash memory devices, or one or more other non-volatile solid state storage devices. The memory 306, or alternatively the non-volatile memory within the memory 306, includes a non-transitory computer readable storage medium. In some implementations, the memory 306, or the non-transitory computer readable storage medium of the memory 306, stores the following programs, modules, and data structures, or a subset or superset thereof: operating logic 320 including procedures for handling various basic system services and for performing hardware dependent tasks; a device communication module 322 for connecting to and communicating with other network devices (e.g., network interface 160, such as a router that provides Internet connectivity, networked storage devices, network routing devices, server system 164, etc.) connected to one or more networks 162 via one or more communication interfaces 304 (wired or wireless); an input processing module 326 for detecting one or more user inputs or interactions from the one or more input devices 314 and interpreting the detected inputs or interactions; a user interface module 328 for providing and displaying a user interface in which settings, captured data, and/or other data for one or more devices (e.g., the smart device 204, and/or other devices in smart-home environment 100) can be configured and/or viewed; one or more applications 330 for execution by the smart device (e.g., games, social network applications, smart home applications, and/or other web or non-web based applications) for controlling devices (e.g., executing commands, sending commands, and/or configuring settings of the smart device 204 and/or other client/electronic devices), and for reviewing data captured by devices (e.g., device status and settings, captured data, or other information regarding the smart device 204 and/or other client/electronic devices); a device-side module 332, which provides device-side functionalities for device control, data processing and data review, including but not limited to: a command receiving module 3320 for receiving, forwarding, and/or executing instructions and control commands (e.g., from a client device 220, from a server system 164, from user inputs detected on the user interface 310, etc.) for operating the smart device 204; a data processing module 3322 for processing data captured or received by one or more inputs (e.g., input devices 314, image/video capture devices 318, location detection device 316), sensors (e.g., built-in sensors 390), interfaces (e.g., communication interfaces 304, radios 340), and/or other components of the smart device 204, and for preparing and sending processed data to a device for review (e.g., client devices 220 for review by a user); device data 334 storing data associated with devices (e.g., the smart device 204), including, but is not limited to: account data 3340 storing information related to user accounts loaded on the smart device 204, wherein such information includes cached login credentials, smart device identifiers (e.g., MAC addresses and UUIDs), user interface settings, display preferences, authentication tokens and tags, password keys, etc.; local data storage database 3342 for selectively storing raw or processed data associated with the smart device 204 (e.g., video surveillance footage captured by a camera 118); a bypass module 336 for detecting whether radio(s) 340 are transmitting signals via respective antennas coupled to the radio(s) 340 and to accordingly couple radio(s) 340 to their respective antennas either via a bypass line or an amplifier (e.g., a low noise amplifier); and a transmission access module 338 for granting or denying transmission access to one or more radio(s) 340 (e.g., based on detected control signals and transmission requests).

Each of the above identified elements may be stored in one or more of the previously mentioned memory devices, and corresponds to a set of instructions for performing a function described above. The above identified modules or programs (i.e., sets of instructions) need not be implemented as separate software programs, procedures, or modules, and thus various subsets of these modules may be combined or otherwise rearranged in various implementations. In some implementations, the memory 306, optionally, stores a subset of the modules and data structures identified above. Furthermore, the memory 306, optionally, stores additional modules and data structures not described above.

FIGS. 4A-4B are perspective views of a representative camera assembly in accordance with some implementations. FIG. 4A shows a first perspective view of a representative camera 118. As shown in FIG. 4A, the camera 118 includes a head assembly 403, a stand assembly 402, and a cable 414 (e.g., for powering the camera 118 and/or transferring data between the camera 118 and a second electronic device.). The head assembly 403 includes a cover element 404 and a casing 401 (also sometimes called a housing). In accordance with some implementations, the cover element 404 has IR transparent portions 412 for IR illuminators, visible and IR transparent portion 416 for an image sensor, and semi-transparent portions 410 (corresponding to an ambient light sensor) and 408 (corresponding to a status LED). In accordance with some implementations, the cover element 404 also includes apertures 406 for microphones. In accordance with some implementations, the casing 401 includes an aperture 406-3 for a microphone.

In some implementations, the casing 401 has two or more layers. In some implementations, the inner layer is composed of a thermally conductive resin. In some implementations, the outer layer is a structural jacket configured to protect the camera 118 from environmental conditions such as moisture or electromagnetic charge (e.g., static electricity). In some implementations, the structural jacket is configured to protect the camera 118 from impacts, such as from a collision with another object or the ground.

FIG. 4B shows a back view of the camera 118. As shown in FIG. 4B the cable 414 is detachable from the stand assembly 402. For example, a user may store the cable 414 separately from the camera 118 when desired. In accordance with some implementations, the casing 401 includes a plurality of apertures 417 for a speaker.

Figure 5A:
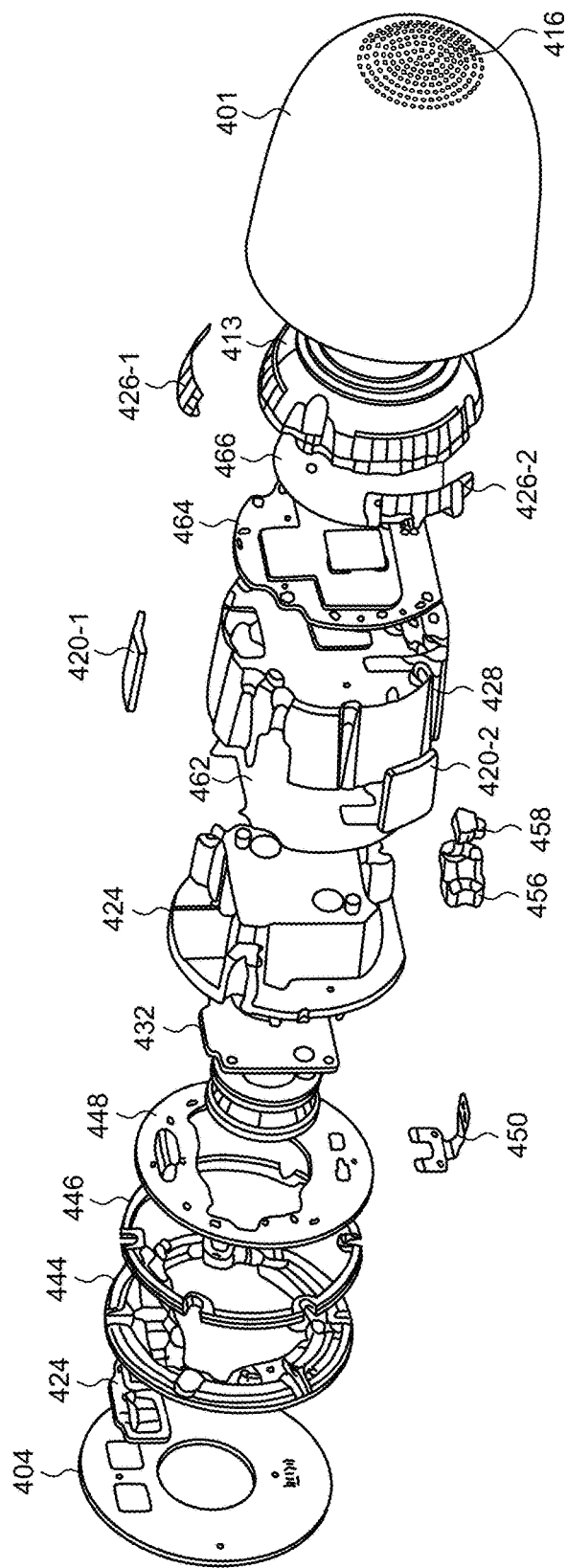
FIG. 5A is an expanded component view of a representative camera assembly in accordance with some implementations.
Figure 5B:
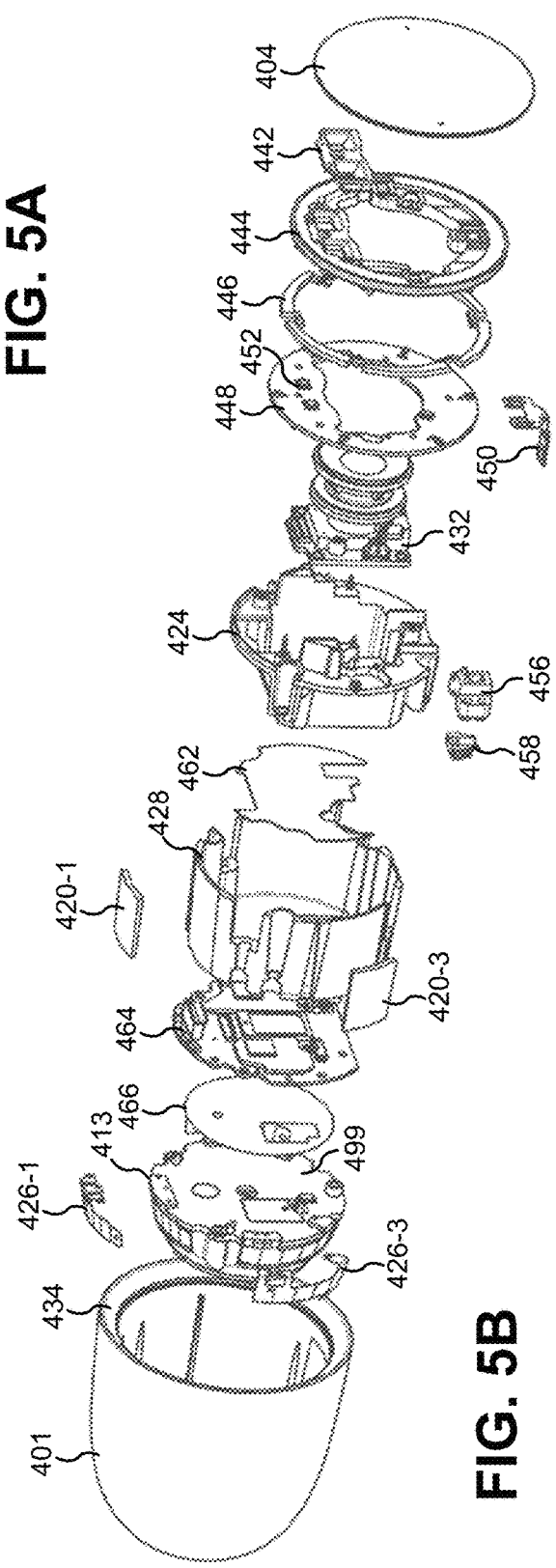
FIG. 5B is an expanded component view of a representative camera assembly in accordance with some implementations.

FIGS. 5A-5B are expanded component views of a representative camera assembly in accordance with some implementations. The camera 118 includes a cover element 404, an image sensor assembly 432, a speaker assembly 413, and a main circuit board 464. In some implementations, the speaker assembly 413 includes a speaker and a heat sink. In some implementations, the heat sink is configured to dissipate heat generated at the main board 464. In some implementations, the speaker assembly 413 acts as a heat sink for the camera's system-on-a-chip (SoC). In some implementations, the SoC is thermally coupled to the speaker assembly 413 with a thermal pad. In some implementations, the thermal pad's area is smaller than the speaker assembly's bottom surface 499. For optimal heat dissipation it is beneficial to spread the heat from the thermal pad over the entire bottom surface of the speaker assembly. In some implementations, a thermally graphite sheet (e.g., thermally conductive sheet 466) is used to achieve this spreading since graphite has very high in-plane thermal conductivity.

In some implementations, the camera 118 is a video streaming device with powerful computing capability embedded in the device. Therefore, in some instances, it will consume a lot of power and will also generate a lot of heat. In order to prevent the chipset and other components from being damaged by the heat, a thermal relief solution includes directing the heat from the CPU (e.g., a CPU of the SoC) to the speaker assembly 413. In some implementations, the speaker assembly 413 is composed of a thermally conductive plastic that is structurally suitable and has good heat spreading properties. In some implementations, a thermal pad on top of the shield can is used to direct the heat to the speaker assembly. To further distribute the heat onto the speaker, in some implementations, a graphite sheet is placed on the bottom surface of the speaker assembly. In some implementations, the size of the graphite sheet is maximized to achieve the best thermal relief function.

The camera 118 includes the cover element 404 having the IR transparent portions 412 for IR illuminators, the apertures 406 for microphones, the semi-transparent portion 408 corresponding to a status LED, and the semi-transparent portion 410 corresponding to an ambient light sensor. The camera 118 also includes a plurality of heat pads 420 for dissipating heat from the main board 464 and a thermal receiver structure 428 (e.g., having a shape like that of a fryer pot, hereinafter referred to as "fryer pot 428") to the casing 401, a plurality of antennas 426 for wirelessly communicating with other electronic devices, a thermal mount structure 424 (e.g., having a shape like that of a fryer basket, hereinafter referred to as "fryer basket 424") for dissipating and transferring heat from the image sensor assembly 432 to the cover element 404, and pads for thermally isolating the fryer basket 424 from the fryer pot 428.

In some implementations, the heat pads 420 are adapted to transfer heat from the fryer pot 428 to the casing 401. In some implementations, the heat pads 420 are adapted to thermally couple an inner layer of the casing 401 and the fryer pot 428. In some implementations, the heat pads are composed of a plastic. In some implementations, the heat pads are adapted to thermally de-couple the fryer basket 424 from the fryer pot 428. In some implementations, the fryer basket 424 is composed of magnesium. In some implementations, the fryer basket 424 is adapted to dissipate heat from the image sensor assembly 432. In some implementations, the fryer basket 424 is adapted to provide structural support to the camera 118. In some implementations, the fryer basket 424 is adapted to protect the image sensor assembly 432 from environmental forces such as moisture and/or impact from objects and/or the ground.

In some implementations, the antennas 426 are configured to operate concurrently using two distinct frequencies. In some implementations, the antennas 426 are configured to operate concurrently using two distinct communication protocols. In some implementations, one or more of the antennas 426 is configured for broadband communications (e.g., Wi-Fi) and/or point-to-point communications (e.g., Bluetooth). In some implementations, one or more of the antennas 426 is configured for mesh networking communications (e.g., ZWave). In some implementations, a first antenna 426 (e.g., antenna 426-1) is configured for 2.4 GHz Wi-Fi communication and a second antenna 426 (e.g., antenna 426-2) is configured for 5 GHz Wi-Fi communication. In some implementations, a first antenna 426 (e.g., antenna 426-1) is configured for 2.4 GHz Wi-Fi communication and point-to-point communication, a second antenna 426 (e.g., antenna 426-2) is configured for 5 GHz Wi-Fi communication and point-to-point communication, and a third antenna 426 (e.g., antenna 426-3) is configured for mesh networking communication. In some implementations, two or more of the antennas 426 are configured to transmit and/or receive data concurrently with others of the antennas 426. MIMO (multi input multi output) provides the benefit of greater throughput and better range for the wireless communication.

One of the parameters in the antenna system is the isolation between two antennas. Better isolation can ensure the data transmitted through two antennas are uncorrelated which is the key to the MIMO system. One way to achieve good isolation is to have large antenna separations. However, in modern consumer electronics the space left for antennas is very tight so having enough spacing between antennas is infeasible. While isolation is important, the antenna efficiency cannot be sacrificed. Isolation is directly related to how much energy is coupled from one antenna to another. The Friis equation defines the power received by another antenna as inversely proportional to $(1/R)^2$, where R is the distance between two antennas. So increasing antenna spacing is one effective way to achieve good isolation. Another means to achieve isolation is through use of a decoupling network. For example, an artificial coupling channel is generated in additional to its original coupling channel (e.g., which is through air). By properly managing the two coupling channels, the good isolation can be achieved.

In some implementations, the antennas 426 include at least one dual-band Inverted-F Antenna (IFA). In some implementations, the antennas are made by FPC, LDS, Stamping, or other state of art antenna manufacturing technology. In some implementations, the fryer pot 428 is a system ground for one or more of the antennas 426. In some implementations, the size of the antenna is about quarter-wavelength at 2.4 GHz. In some implementations, each antenna includes a radiating element, a feed line, and a ground stub. The ground stub presents an inductance to compensate for capacitance generated between the radiating element and the fryer pot 428. In some implementations, at least one of the antennas 426 includes a second ground stub. The second ground stub is adapted to match the antenna to both 2.4 GHz and 5 GHz. In some implementations, the antenna feed is the feeding point for the 2.4 GHz and 5 GHz WiFi signal. In some implementations, the feed point is connected to the output of a WiFi chip. In some implementations, the antennas 426 include two identical IFA antennas. Both antennas are attached to the speaker assembly 413.

In some implementations, at least one of the antennas 426 includes a second type of antenna having first radiating element, a second radiating element, a first ground stub, and second ground stub. In some implementations, the size of the first radiating element is around quarter wavelength of 5 GHz. In some implementations, the resonance frequency at 2.4 GHz is determined by: (i) the size of the second radiating element, (ii) the position of the first ground stub, and (iii) the position of the second ground stub. In some implementations, the first ground stub is placed at a pistol end of the second radiating element. In some implementations, the second ground stub is between the first radiating element and the first ground stub. In some implementations, the position where second ground stub is attached to the second radiating element is adjusted to tune to the resonant frequency at 2.4 GHz. In some implementations, the first ground stub not only acts as part of the antenna, but also a shielding element that can reduce coupling coming from the left-handed side of the first ground stub. In some implementations, the second ground stub is also a shielding element to further reduce the coupling coming from the left handed side of the antenna. In some implementations, the second type of antenna includes more than 2 ground stubs. By using more ground stubs the antenna's physical size can be enlarged while maintaining the same resonant frequency (e.g., 2.4 GHz). In some implementations, the first and second ground stubs are on the right-handed side of the first radiating element to reduce coupling coming from the right-handed side. In some implementations, the antennas 426 include one or more antennas of a first type (e.g., IFAs) and one or more antennas of the second type.

By using a set of antennas including both a first type of antenna (e.g., an IFA) and the second type of antenna, two antennas can be positioned in a tight space while maintaining both good efficiency and good isolation between them.

This enables the camera 118 to be compact without sacrificing the quality of wireless connectivity. In some implementations, both types of antennas are manufactured by conventional FPC technology with low cost. Unlike an antenna system relying on a decoupling system to achieve a similar isolation level, the IFA and second type antennas can be optimized and/or tuned independently.

The camera 118 may include the cover element 404, casing 401 with speaker holes 417, the image sensor assembly 432, and a speaker assembly 413. In some implementations, as shown, the speaker holes 417 extend directly outward from the speaker, which results in holes with an elliptical outer surface. In some implementations, the speaker holes 417 are parallel to one another. In some implementations, the speaker holes 417 extend outward at an angle consistent with the rear surface of the casing 401 such that the holes have a circular, rather than elliptical, outer surface (not shown). The camera 118 also includes a light guide 434 for directing light from a light assembly out the face of the camera 118.

The camera 118 includes an infrared (IR) reflector 442, a light diffuser 444, a light guide 446, a light ring 448, a microphone assembly 450, the image sensor assembly 432, the fryer basket 424, stand coupling elements 456 and 458, the fryer pot 428, a thermal insulator 462 adapted to thermally isolate the fryer pot 428 from the fryer basket 424, the main board 464, the thermally conductive sheet 466, the antennas 426, the speaker assembly 413, and the casing 401. In accordance with some implementations, the casing 401 has a lip 434 for reflecting and directing light from the light diffuser 444 outward from the face of the camera 118.

In some implementations, the cover element 404 comprises a chemically-strengthened glass. In some implementations, the cover element 404 comprises a soda-lime glass.

In some implementations, the image sensor assembly 432 includes a circuit board (e.g., a PCB board), an IR cut filter, a lens holder, and an image sensor. In some implementations, the image sensor comprises a 4 k image sensor. In some implementations, the image sensor comprises a 12 megapixel sensor. In some implementations, the image sensor comprises a wide-angle lens.

In some implementations, the thermally conductive sheet 466 is adapted to dissipate heat generated by the main board 464 and/or transfer heat from the main board 464 to the speaker assembly 413 for subsequent dissipation outside of the camera via the rear portion of the casing 401. In some implementations, the conductive sheet 466 is a graphite sheet. When a graphite sheet is placed near the antenna system with multiple antennas, it can create a coupling medium between antennas. The increased coupling caused by the graphite can decrease the isolation between two antennas, thus degrading antenna efficiency or causing permanent damage to the chipset.

In some implementations, the antennas 426 are configured to enable the camera 118 to wirelessly communication with one or more other electronic devices, such as a hub device 180, a smart device 204, and/or a server system 164.

In some implementations, the fryer pot 428 is composed of magnesium. In some implementations, the fryer pot 428 is adapted to provide structural support to the camera 118.

In some implementations, the fryer pot 428, the main board 464, the conductive sheet 466, the speaker assembly 413, and the antennas 426 comprise a rear sub-assembly. Thermally de-coupling the fryer basket 424 from the fryer pot 428 prevents heat generated by the main board 464 from interfering with the image sensor assembly 432. In accordance with some implementations, heat generated by the front of the main board 464 is transferred to the fryer pot 428 to the heat pads 420 and dissipated outside of the camera via the casing 401 (e.g., the sides of the casing). In accordance with some implementations, heat generated by the back of the main board 464 is transferred to the thermally conductive sheet 466 to the speaker assembly 413 and dissipated outside of the camera via the back portion of the casing 401.

In some implementations, the rear sub-assembly is affixed to the casing 401 via one or more fasteners (e.g., via 2-3 screws). In some implementations, the cover element 404, the infrared reflector 442, the light diffuser 444, the light guide 446, the light ring 448, and the image sensor assembly 432 comprise a front sub-assembly. In some implementations, the front sub-assembly is affixed to the casing 401 via one or more fasteners (e.g., 2-3 screws). In some implementations, the front sub-assembly is affixed to the rear sub-assembly via one or more fasteners.

In some implementations, the fryer basket 424 is adapted to dissipate heat generated by the image sensor assembly 432 and/or the light ring 448. In some implementations, the fryer basket 424 includes one or more forward-facing microphones. In some implementations, the downward-facing microphone 450 is operated in conjunction with the microphones on the fryer basket 424 to determine directionality and/or location of incoming sounds.

In some implementations, the IR reflector 442 is coated with an IR and/or visible light reflective coating. In some implementations, the IR reflector 442 is adapted to direct light from the IR illuminators 452 to a scene corresponding to a field of view of the image sensor assembly 432.

In some implementations, the light ring 448 comprises a plurality of visible light illuminators (e.g., RGB LEDs), a plurality of IR illuminators 452, and circuitry for powering and/or operating the visible light and/or IR illuminators. In some implementations, the light guide 446 is adapted to direct light from the visible light illuminators out the face of the camera 118. In some implementations, the light guide 446 is adapted to prevent light from the visible light illuminators from entering the image sensor assembly 432. In some implementations, the light guide 446 is adapted to spread the light from the visible light illuminators in a substantially even manner. In some implementations, the light guide 446 is composed of a clear material. In some implementations, the light guide 446 is composed of a poly-carbonite material. In some implementations, the light guide 446 has a plurality of dimples to refract the light from the illuminators and prevent the light from entering the image sensor assembly 432. In some implementations, the light guide 446 is adapted to provide more uniform color and light output to a user from the illuminators. In some implementations, the light guide 446 includes a plurality of segments, each segment corresponding to a visible light illuminator. In some implementations, the light guide 446 includes one or more light absorbing elements (e.g., black stickers) arranged between each segment to prevent light leakage from one illuminator segment to another illuminator segment.

In some implementations, the light diffuser 444 includes two or more sections (e.g., an inner section and an outer section). In some implementations, the light diffuser 444 is adapted to diffuse the light from the visible light illuminators. In some implementations, the light diffuser 444 is adapted to direct the light from the illuminators toward the lip 434 of the casing 401. In some implementations, the light ring 448 (and corresponding elements such as the light guide 446 and/or light diffuser 444) causes a circular colored (or white) light to be emitted from the front of the camera 118.

In some implementations the components and corresponding light are circular and arranged around the periphery of the front of the camera 118. They may encircle all or substantially all elements of the camera 118, such as the image sensor assembly 432, the IR illuminators 452, the ambient light sensor 451, a status LED, and the microphone apertures 406. In other implementations, they are arranged not around the periphery but rather at an inner diameter, e.g., around only the image sensor assembly 432. In yet other implementations, they do not surround any front-facing element of the camera 118. In some implementations, they are arranged in a non-circular shape, such as a square, oval, or polygonal shape. In some implementations, they are not arranged on the front of the device but rather a different surface of the device, such as the bottom, top, sides, or back. In some implementations, multiple such light rings and components are arranged onto the same or different surfaces of the camera 118.

The light ring 448 (and corresponding elements) may operate to indicate a status of the camera 118, another device within or outside of the smart home environment 100 (e.g., another device communicatively coupled either directly or indirectly to the camera 118), and/or the entire connected smart home environment 100 (e.g., system status). The light ring 448 (and corresponding elements) may cause different colors and/or animations to be displayed to a user that indicate such different statuses.

For example, in the context of communicating camera 118 status, when the camera 118 is booting for the first time or after a factor reset, the ring may pulse blue once at a slow speed. When the camera 118 is ready to begin setup, the ring may breathe blue continually. When the camera 118 is connected to a remote cloud service and provisioning is complete (i.e., the camera is connected to a user's network and account), the ring may pulse green once. When there is a service connection and/or provisioning failure, the ring may blink yellow at a fast speed. When the camera 118 is being operated to facilitate two-way talk (i.e., audio is captured from the audio and communicated to a remote device for output by that remote device simultaneously with audio being captured from the remote device and communicated to the camera 118 for output by the camera 118), the ring may breathe blue continuously at a fast speed. When the camera 118 is counting down final seconds before a factory reset, the ring may close on itself at a rate equal to the time until reset (e.g., five seconds). When the camera 118 has been factory and while the setting are being erased the ring may rotate blue continuously. When there is insufficient power for the camera 118 the ring may blink red continuously at a slow speed. The visual indications are optionally communicated simultaneously, concurrently, or separately from audio indications that signal to the user a same or supplemental message. For example, when the camera 118 is connected to a remote cloud service and provisioning is complete (i.e., the camera is connected to a user's network and account), the ring may pulse green once and output an audio message that "remote cloud service and provisioning is complete."

Additionally or alternatively, the camera 118 may communicate the status of another device in communication with the camera 118. For example, when a hazard detector 104 detects smoke or fire sufficient to alarm, the camera 118 may output a light ring that pulses red continuously at a fast speed. When a hazard detector 104 detects smoke or fire sufficient to warn a user but not alarm, the camera 118 may output a light ring that pulses yellow a number of times. When a visitor engages a smart doorbell 106 the camera 118 may output a light ring depending on the engagement; e.g., if the smart doorbell 106 detects motion, the camera 118 may output a yellow light ring, if a user presses a call button on the smart doorbell 106, the camera 118 may output a green light ring. In some implementations, the camera 118 may be communicatively coupled to the doorbell 106 to enable audio communication therebetween, in which case an animation and/or color of the light ring may change depending on whether the user is speaking to the visitor or not through the camera 118 or another device.

Additionally or alternatively, the camera 118 may communicate the cumulative status of a number of network-connected devices in the smart home environment 100. For example, a smart alarm system 122 may include proximity sensors, window break sensors, door movement detectors, etc. A whole home state may be determined based on the status of such a plurality of sensors/detectors. For example, the whole home state may be secured (indicating the premises is secured and ready to alarm), alarming (indicating a determination that a break-in or emergency condition exists), or somewhere in between such as pre-alarming (indicating a determination that a break-in or emergency condition may exist soon or unless some condition is satisfied). For example, the camera 118 light ring may pulse red continuously when the whole home state is alarming, may pulse yellow when the whole home state is pre-alarming, and/or may be solid green when the whole home state is secured. In some implementations, such visual indications may be communicated simultaneously (or separately from) with audio indications that signal to the user the same or supplemental message. For example, when the whole home state is alarming, the ring may pulse red once and output an audio message that indicates the alarm "alarm". In some implementations, the audio message may provide supplemental information that cannot be conveyed via the light ring. For example, when the whole home state is alarming due to a basement window being broken, the audio message may be "alarm—your basement window has been broken." For another example, when a pre-alarm amount of smoke has been detected by a hazard detector 104 located in the kitchen, the audio message may be "warning—smoke is detected in your kitchen."

In some implementations, the camera 118 may also or alternatively have a status LED. Such a status LED may be used to less-instructively communicate camera 118, other device, or multiple device status information. For example, the status light may be solid green during initial setup, solid green when streaming video and/or audio data normally, breathing green when someone is watching remotely, solid green when someone is watching remotely and speaking through the camera 118, and off when the camera 118 is turned off or the status LED is disabled. It should be appreciated that the status LED may be displayed simultaneously with the light ring. For example, the status LED may be solid green during setup while the light ring breathes blue, until the end of setup when the device is connected to the service and provisioning is complete whereby the status LED may continue to be solid green while the light ring switches to a single pulse green.

Video Monitoring of a Subject with Exaggerated Playback

The camera 118 described above in detail has many different uses in the smart-home environment. In the context of a security system, the camera 118 can detect human presence and/or motion, and can provide a real-time video feed of the monitored area to a user's smart phone or other mobile computing device. In a hazard-detection scenario, the camera 118 can provide a real-time video feed of a situation in which a hazard might exist. For example, if smoke is detected within the smart-home environment, the camera 118 can provide a view to show areas of the environment that may be affected by the fire or smoke. The camera 118 can be used to determine whether the alarm is a false alarm or an alarm situation to which a response may be required. A single camera 118 or set of cameras can be installed in a smart-home environment, and they can be put to many different simultaneous uses. For example, a single camera can be part of a home security system and part of a hazard detection system at the same time. One of the many uses to which the camera 118 can be simultaneously employed is that of monitoring any infant or other subject within the smart-home environment.

Many parents find comfort in being able to monitor their sleeping infant in real time. Video monitoring systems are available that provide a live video feed of an infant in their sleep environment. These live video feeds are traditionally sent through an RF frequency communication system to a dedicated video monitor or console that can be plugged in at different locations in the user's home. However, these traditional infant monitoring systems that employ live video feeds suffer from a number of drawbacks. First, these traditional systems typically employ a low resolution camera. The resultant video feed is typically grainy, and it is impossible to view small motions of the infant. Second, these cameras are typically unable to provide any additional information other than the live video feed itself. The live video feed provides very little information on the health and/or safety condition of the infant. Moreover, because there is no interactivity in these traditional video feeds, these baby monitors do not provide any meaningful emotional connection between the user and the infant.

In order to solve these and other technical problems, the embodiments described herein use the camera 118 with its high-resolution live video feed to perform additional processing on the live video feed itself. This processing can extract vital signs from the infant based at least in part on the on the observed motions in the video feed. For example, the camera can process the live video feed to identify small motions of the monitored subject. The camera can also filter out large motions that are not indicative of vital signs, such as users walking in front of the camera, or non-monitored subjects moving in the room. The relatively small motions that are detected by the video camera can be encoded in a pixel-by-pixel displacement image that records a directional displacement for each pixel in each frame relative to a baseline setting. In some embodiments, the live video feed and the displacement image can be transmitted through a remote server to a user's mobile device. The mobile device can present an exaggerated representation of the small motions identified by the camera 118. For example, the displacement image can be scaled by a scaling factor to exaggerate the breathing motions of an infant. An electronic display of the user's mobile computing device can then display the live video feed with the video motion of the infant breathing being exaggerated in real-time. For example, a video of the rise and fall of the infant's chest can be exaggerated such that it is easily observable on the screen of the mobile device. In some implementations, other exaggerated representations of the recorded small motions of the infant or monitored subject can also be presented on the mobile device, such as a graphic animation that moves according to a detected heartbeat or breathing pattern. Some implementations may provide a tactile response, such as a vibration with a magnitude and timing that corresponds to a heartbeat and/or breathing pattern. Some implementations may additionally or alternatively provide audible responses, such as simulated breathing sounds or heartbeats that coincide with the detected vital signs of the monitored subject.

Throughout this disclosure, the monitoring system may use the monitoring of an infant as an example. However, other embodiments are not limited to an infant in a sleep environment. Some embodiments may monitor other types of subjects, such as the elderly, the physically disabled, and/or other human subjects. These subjects may also be monitored in any environment aside from a sleep environment. For example, a subject could be monitored in a wheelchair, in a swimming pool, in a bed, in a recliner, on a couch, and/or any other environment. Although the camera 118 described above is also used as an example, other embodiments may use different home video cameras that are configured to capture a live video feed of the monitored subject. Additionally, the exaggerated representations that are provided at the user's computing device can be received on any type of computing device, and may include any type of representation in which the detected small movements of the monitored subject are presented in an exaggerated or simulated fashion.

Figure 6:
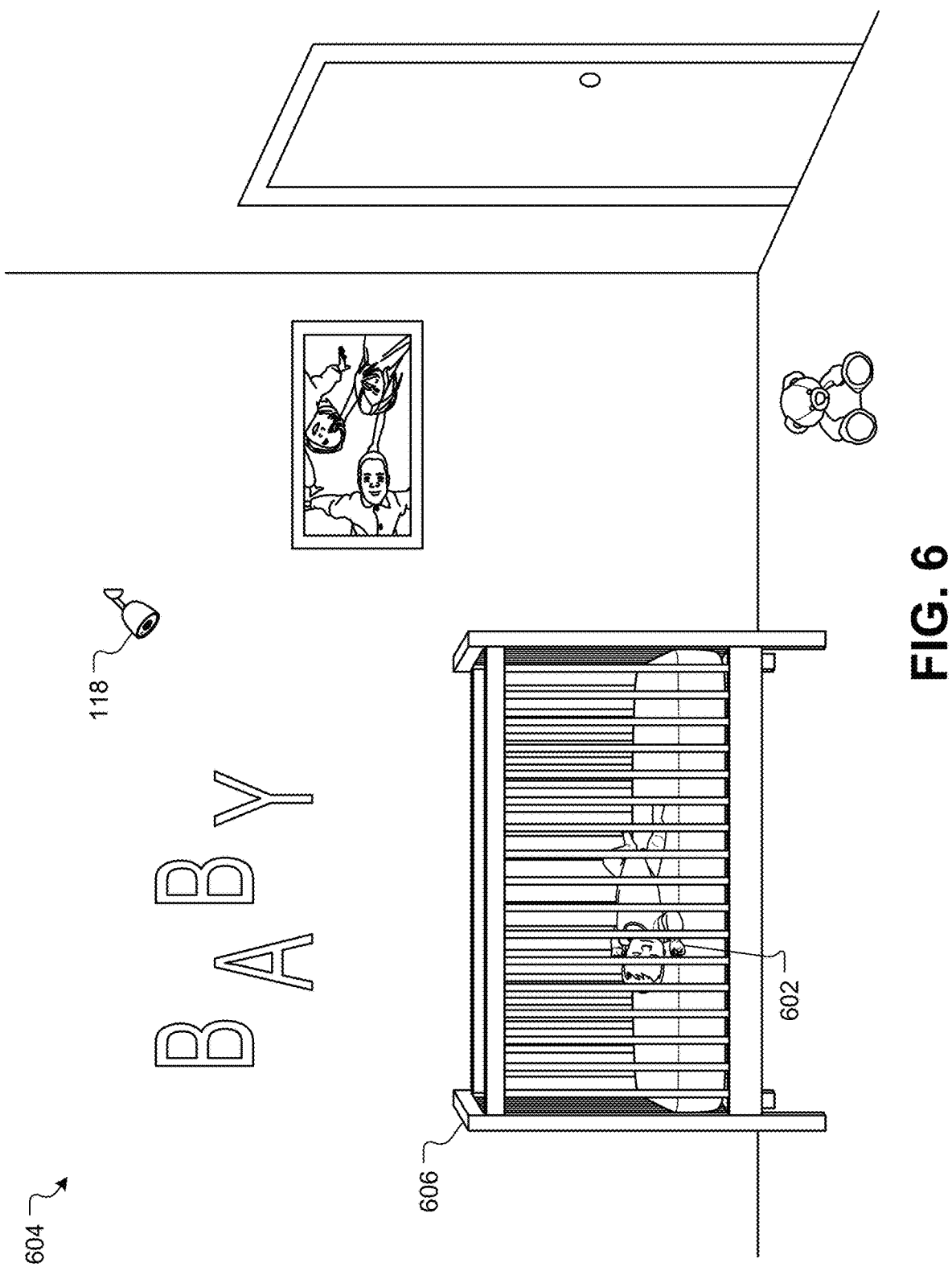
FIG. 6 illustrates an infant sleeping in a sleep environment and being monitored by a camera, according to some embodiments.

FIG. 6 illustrates an infant 602 sleeping in a sleep environment 604 and being monitored by a camera 118, according to some embodiments. The camera 118 can be one of many video cameras that are distributed throughout the smart-home environment. Although not depicted explicitly in FIG. 6, the sleep environment 604 may also include additional cameras, some of which may also be positioned to observe the infant 602. Other cameras may be used for security purposes or may be configured to observe the infant 602 in other positions and/or other locations within the sleep environment 604.

The sleep environment 604 may include a bedroom, a closet, a nook, and/or any other location within the smart-home environment. The sleep environment may be characterized in that it includes a bed, a crib 606, a couch, a sofa, a porta-crib, a mattress, a sleeping pad, an air mattress, a covered section of the floor, and/or any other sleep-suitable location. Although the infant 602 is depicted in FIG. 6, any other monitored subject may also be monitored by the camera 118 and used in conjunction with the algorithms described in detail below. Other subjects may be monitored in sleep environments and/or any other type of monitored environment within the smart-home environment.

In this example, the camera 118 is positioned within the sleep environment 604 such that a live video feed of the infant 602 can be captured. Some embodiments may include automatic pan/tilt mounts that use computer vision algorithms to automatically train the camera 118 on the infant 602 such that the infant 602 can be located anywhere in the sleep environment 604 and still be monitored by the camera 118. In some embodiments, the pan/tilt mounts can be driven by motion detection algorithms in the camera, such that they focus on motion detected in their field-of-view. Some embodiments may use one or more cameras that are trained specifically on different locations within the sleep environment 604, such as the crib 606, the floor, a changing table, and/or the like. Each of these cameras may be activated when movement is detected within their field of view. Therefore, when the infant 602 is placed in the crib 606, the camera 118 can automatically detect the shape and/or movement of the infant 602 and determine that the infant 602 is within its field of view. Camera 118 can then automatically begin recording, analyzing, and/or transmitting a live video feed of the infant 602.

Figure 7:
FIG. 7 illustrates a view of the infant that may be received by the camera, according to some embodiments.

FIG. 7 illustrates a view of the infant 602 that may be received by the camera 118, according to some embodiments. In many situations, the infant 602 may be relatively immobile while sleeping. For example, the infant 602 may be confined to the crib 606 while sleeping. Therefore, the field of view of the camera 118 may be adjusted or shrunk to capture in high resolution only the area in which the infant 602 may occupy in the sleep environment. This may include automatically panning/tilting the camera to center its field of view on the infant 602. Additionally and/or alternatively, a zoom of the camera 118 can be adjusted such that the infant 602 substantially fills the field-of-view of the camera 118. For example, the zoom of the camera may be adjusted until the infant 602 fills approximately 50% of the field of view of the camera 118.

The camera 118 described in detail above includes, for example, a 4 k resolution. This level of resolution may be sufficient to capture small motions 702 of the infant 602. These small motions 702 may include the rhythmic up-and-down motions of the chest of the infant 602 while breathing. The small motions 702 may also include the rhythmic motions of the chest of the infant 602 resulting from the heartbeat of the infant 602. These small motions 702 are often very subtle and difficult to see over a live video feed on a small screen. With existing technologies, it is simply impossible for a traditional baby monitor to provide a camera and monitor combination with sufficient resolution to make the small motions 702 visible to an observer. However, the camera 118 described herein includes sufficient resolution to detect and later display the small motions 702 on a mobile device of the user as described below.

Figure 8:
FIG. 8 illustrates a view of the infant with a bounding box that reduces the processing power, memory, and/or bandwidth required by the system, according to some embodiments.

FIG. 8 illustrates a view of the infant 602 with a bounding box 802 that reduces the processing power, memory, and/or bandwidth required by the system, according to some embodiments. Some embodiments may analyze the real-time video feed of the infant 602 at the camera 118. In these embodiments, it may be advantageous to decrease the number of pixels that need to be analyzed in the full field-of-view of the camera 118. By reducing the analyzed portion of the field-of-view of the camera 118, algorithms can run faster and less memory can be used on the camera 118. This may be particularly advantageous for cameras that have relatively small processing capabilities and/or relatively limited memory storage available.

In some embodiments, the video feed of the camera can be analyzed in real time to identify a portion of each image frame that includes the small motions 702. A bounding box 802 can be selected that includes the small motions 702, along with a predetermined amount of each surrounding image. For example, a bounding boxing 802 can include the small motions 702 at the center of the bounding box 802, and can also expand to include an additional two feet of image extending outward from the small motions 702. In other embodiments, the bounding box 802 can include the small motions 702, as well as a surrounding area that can be visually identified as a subject (e.g. the infant 602). In the example of FIG. 8, the bounding box 802 includes the small motions 702 as well as the infant 602. Computer vision algorithms can be used to identify objects, and these computer vision algorithms can be modified based on this particular environment to identify the shape of the infant 602 in each frame. The bounding boxing 802 can be sized such that the entire infant 602 is captured within the analyzed area for the camera 118.

In addition to bounding the area that will be analyzed by the camera 118, the system can also filter out motions that are not of interest or indicative of vital signs of the monitored subject. For example, some embodiments may filter out large motions that are above a threshold amount of pixel displacement. This would filter out events such as the infant 602 rolling over or moving around the sleep environment. This would also filter out movements by additional subjects, such as a parent walking in the room to check on the infant 602. Because these relatively large motions are not indicative of the monitored vital signs of the infant 602 the system can exclude these motions from its analysis. Although these large motions will be visible in the live video feed itself, they will not contribute to the exaggerated representation of the vital signs that will be presented on the user's mobile device as described below.

In some embodiments, the resolution of the captured video feed can be altered based on the bounding box 802. For example, the camera can record and transmit a lower resolution video image for portions of the image outside of the bounding box 802, while preserving a high-resolution digital image for portions of the video feed that are inside the bounding box 802. This can simplify the video processing of a motion detection algorithm, decrease the bandwidth required to transmit the live video feed in real time, reduce the amount of processing power required to detect the small motions 702 in the live video feed, and/or reduce the amount of memory required to store images and information associated with the live video feed.

Figure 9A:
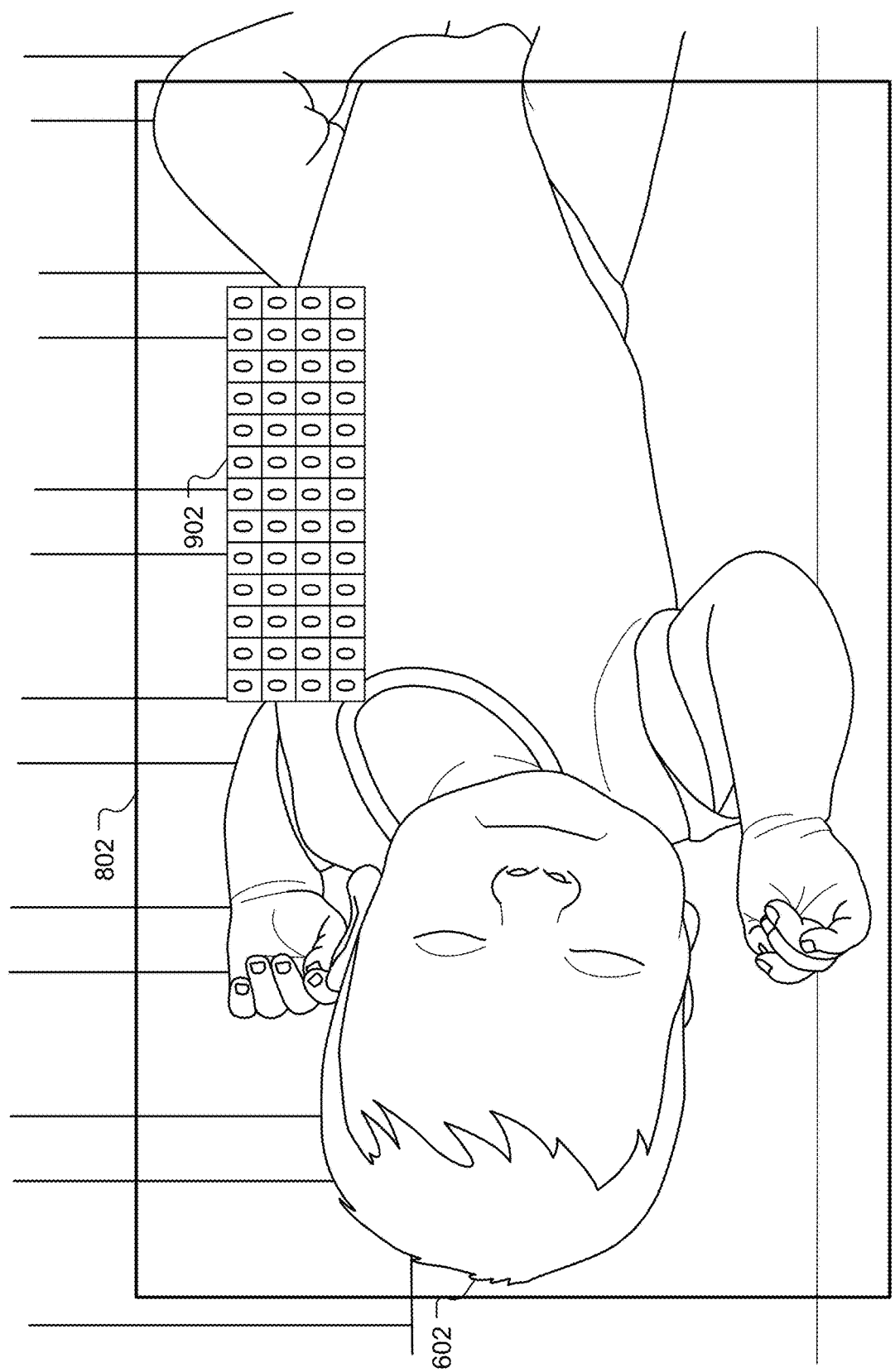
FIG. 9A illustrates a representation of the motion detection analysis that may be performed on each image frame in the live video feed, according to some embodiments.

FIG. 9A illustrates a representation of the motion detection analysis that may be performed on each image frame in the live video feed, according to some embodiments. In this example, an enlarged representation of the pixels 902 in the image captured by the camera 118 is overlaid on the image of the infant 602. The pixels 902 can each be encoded with a number that represents a displacement of each pixel from a baseline position in the image. The position of the infant 602 represents a baseline position that can be used as a reference. Therefore, the values stored in each pixel 902 is "0" in FIG. 9A. Note that the "0" representation is a simplified representation of what is actually stored in each pixel. Some embodiments may include a pixel displacement and a directional indicator that can be used to represent a motion vector or absolute displacement of each pixel. These directional indicators have been omitted from FIG. 9A for clarity. It will also be understood that the pixels 902 are overlaid on the image shown in FIG. 9A merely to illustrate how each pixel location can be associated with a baseline and/or displacement. The numbers in the pixels 902 are not actually displayed or recorded visually by the camera 118.

To determine the baseline pixel locations for the image, a number of different techniques may be used, depending on the particular embodiment. In some embodiments, an initial image captured by the camera 118 can be used as the baseline. In some embodiments, an average location for each pixel can be calculated by averaging the locations of each pixel during a plurality of frames during a moving time window. Some embodiments may assume a rising-and-falling motion of the chest of the infant 602, and may use the lowest location of each pixel in vertical position as a baseline position. Some embodiments may identify positions where the chest of the infant 602 comes to rest, indicating a pause in between breaths. This location may indicate a time when the infant's lungs are relatively empty and therefore useful as a baseline reading. For other vital signs, such as a heartbeat, the baseline can be the relatively still moments between heartbeats.

Some embodiments may detect multiple vital signs, such as a heartbeat and a breathing pattern simultaneously. A frequency analysis can be executed on the pixel displacements in each image to identify different frequency peaks. A relatively rapid frequency peak may identify a heart rate, while a relatively slower frequency peak may identify a breathing rate (i.e., a heart rate will typically be faster than a breathing rate). Frequency filters can then be applied to isolate movements that can be attributed to each vital sign in each frame. Therefore, the analyzed data may include a first set of displacements that are due to, for example, a heart rate and a second set of displacements that are due to a breathing pattern. Other vital signs that can be analyzed by the camera 118 may include the motion of sucking on a pacifier, sucking on a thumb or finger, motions that are indicative of a seizure, and so forth.

Figure 9B:
FIG. 9B illustrates a set of pixels illustrating a relative displacement of pixels in the image of the infant, according to some embodiments.

FIG. 9B illustrates a set of pixels 904 illustrating a relative displacement of pixels in the image of the infant 602, according to some embodiments. As described above, the "0" pixels in FIG. 9A represented a baseline location of each pixel from which subsequent frames can be compared. The motion detection algorithm executed by the camera 118 may include a step of pixel matching in each frame. In other words, each pixel in each subsequent frame can be matched to a corresponding pixel in the baseline image. Various techniques in the field of computer vision processing can be used to track pixels between subsequent frames. After the pixels are tracked, a relative displacement can be calculated between a position of a pixel in the baseline image and a position of the pixel in each subsequent image. The pixel location of a subsequent image can then be encoded with the displacement information. It will also be understood that the pixels 904 are overlaid on the image shown in FIG. 9B merely to illustrate how each pixel location can be associated with a baseline and/or displacement. The numbers in the pixels 904 are generally not actually displayed or recorded visually by the camera 118.

The pixels 904 illustrated in FIG. 9B illustrate a simplified encoding of the displacement information. Specifically, the directional component of each displacement has been omitted for clarity. However, each pixel location shows an absolute displacement distance of the vertical component of each displacement. Some embodiments where it is assumed that the infant 602 is lying on their back, a simple vertical displacement distance may be all the information that needs to be calculated and transmitted from the camera 118. In this example, the number in each pixel location of the pixels 904 indicates a total number of pixel displacements in the vertical direction. Thus, the center portion of the chest may move "3" pixels up, while peripheral portions of the chest may only move "1" pixel up. This image may represent a single frame that is at the peak of a breath that is drawn in by the infant 602. Therefore, the displacements overestimated by FIG. 9B may represent a peak displacement when the lungs of the infant 602 are fully filled. It will be understood that the displacement pixel distances in the pixels 904 are merely provided by way of example and not meant to be limiting. The total pixel displacement may be far larger or smaller depending on the size of the infant 602, the resolution of the camera 118, and/or the distance of the camera 118 from the infant 602.

Figure 10:
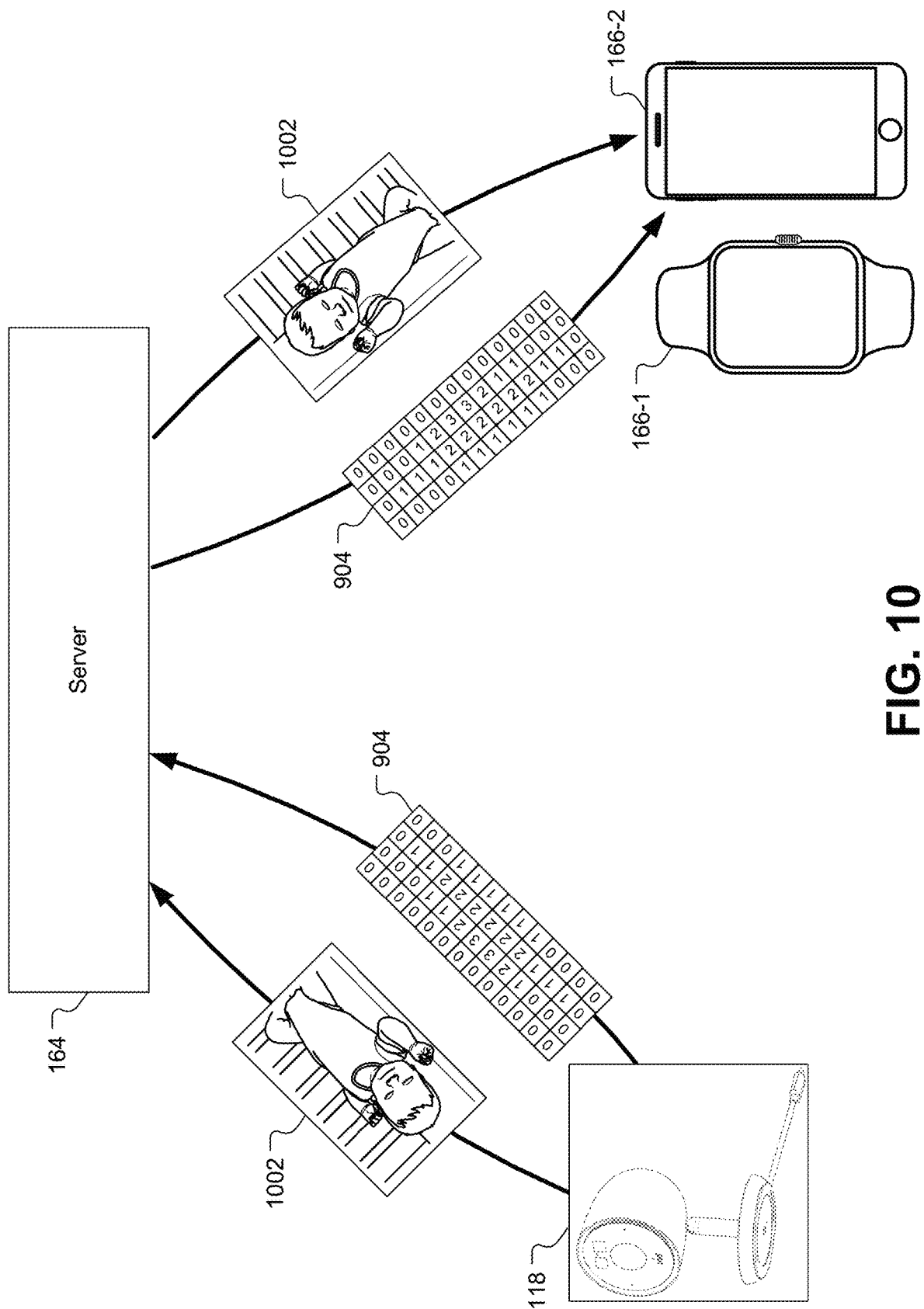
FIG. 10 illustrates a system diagram for processing and transmitting images between the camera and a user's mobile device, according to some embodiments.

FIG. 10 illustrates a system diagram for processing and transmitting images between the camera 118 and a user's mobile device 166, according to some embodiments. In this simplified diagram, some well-understood electronic components may be omitted, such as a power outlet, an ethernet cable, a Wi-Fi home router, and so forth. In some embodiments, the camera 118 can capture a live video feed 1002 of a monitored subject and perform processing operations on the camera 118 itself. As described above, the camera 118 may include one or more processors and one or more memory devices that can be used for executing predefined algorithms on the individual frames of the live video feed 1002. In the example described above, this may include a pixel displacement image with the displacement pixels 904 associated with each frame transmitted by the camera 118. For example, the displacement image that includes the pixels 904 may be represented as a grayscale image where the grayscale color of each pixel indicates displacement distance relative to a baseline position of each pixel.

In some embodiments, only the live video feed 1002 needs to be captured and transmitted from the camera 118. A remote server 164 that is accessible over the Internet through a home Wi-Fi router can also perform the image processing algorithms on the live video feed 1002. In these embodiments, the camera 118 can be a high-resolution camera that does not necessarily need to include processors and memories sufficient to execute the motion detection algorithms described above. The server 164 may include a smart-home device monitoring server that collects monitoring information from smart-home devices in the smart-home environment. The server 164 may also provide data synchronization and/or software upgrades to each of the smart-home devices, including the camera 118, in the smart-home environment. The server 164 can be owned and/or operated by a manufacturer of the smart-home devices, including the camera 118. The server 164 may include a dedicated user account for each smart-home environment (e.g., each home). The server 164 may be referred to herein as a smart-home device monitoring server. The server 164 may also be in communication with computer systems of other entities, such as a utility provider computer system (e.g., an energy utility), a law-enforcement computer system, an emergency-response computer system, and so forth. The server 164 may also include memory locations assigned to each particular user account where a historical record of the live video feed 1002 may be stored and/or archived for later retrieval by the user of the account.

The server 164 can transmit the live video feed 1002 and the pixel displacements 904 to a mobile device 166 of the user associated with the account on the server 164. The mobile device 166 may include a smart watch 166-1, a smartphone 166-2, a laptop computer, a tablet computer, a desktop computer, a personal digital assistant (PDA), an on-board car computer system, a digital home assistant (e.g., Google Home®), and/or any other computing device. In some embodiments, the live video feed 1002 can be transmitted directly from the camera 118 to the mobile device 166 without passing through the server 164, but rather through a local wireless network, such as Bluetooth® network or a proprietary smart-home network (e.g., Thread®). Some embodiments may also transmit only the live video feed 1002 to the mobile device 166 and allow the mobile device 166 to process the live video feed 1002 to detect motion and generate the pixel displacements for the pixels 904. Therefore, the operations described herein for analyzing the live video feed 1002 and generating an exaggerated representation of small motions in the live video feed can be performed at the camera 118, the server 164, the mobile device 166, and/or any other processing system that is part of the smart-home environment.

Figure 11:
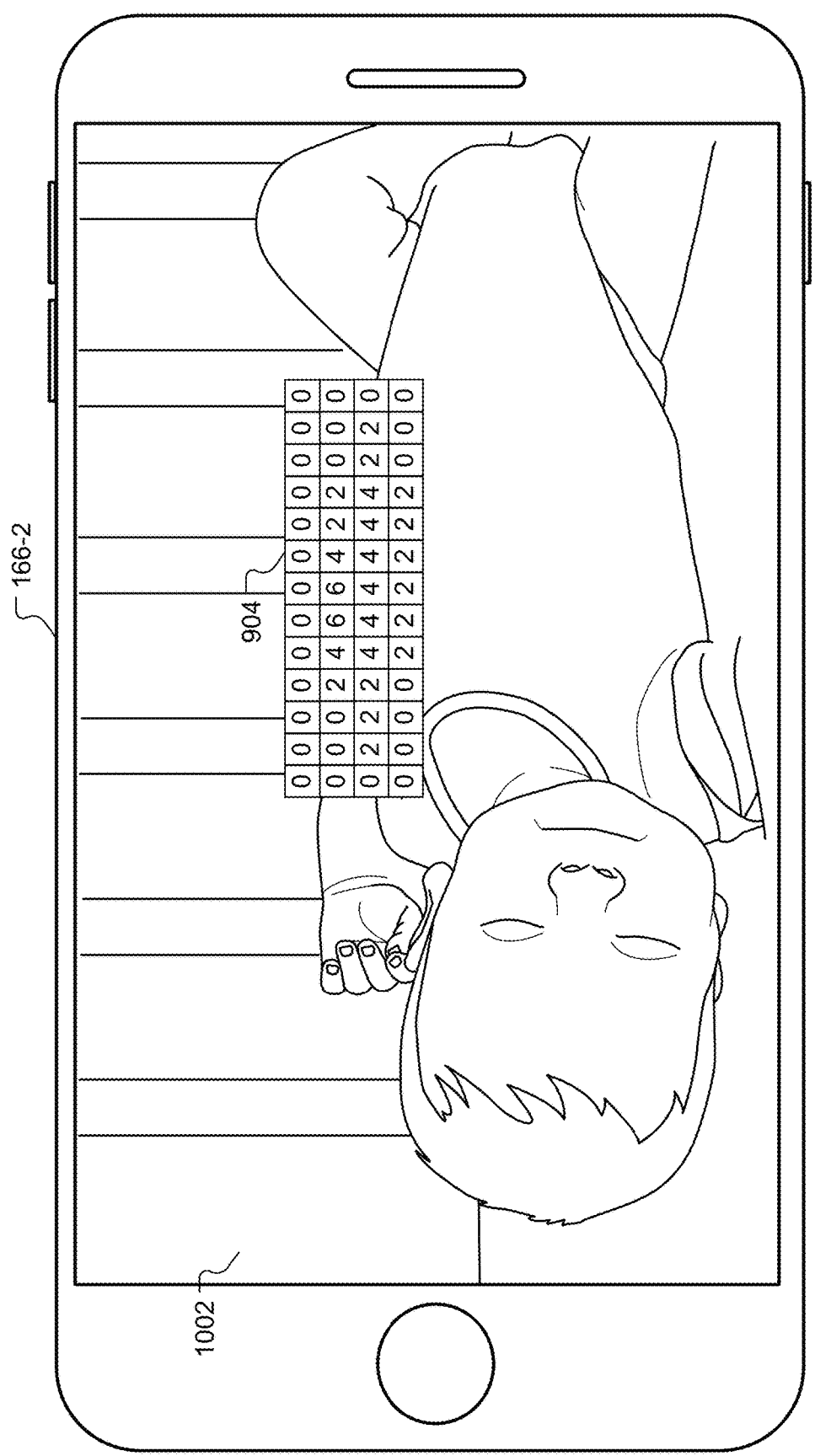
FIG. 11 illustrates a representation of the live video feed displayed on a mobile device, according to some embodiments.

FIG. 11 illustrates a representation of the live video feed 1002 displayed on a mobile device 166-2, according to some embodiments. The displacement pixels 904 are displayed in an overlaid fashion on the live video feed 1002 for illustrative purposes only. The displacement pixels 904 are generally not actually displayed on the mobile device 166-2 in real time. Instead, the live video feed 1002 can be displayed on the screen of the mobile device 166-2 as the user monitors the infant 602. In some cases, the infant 602 may be monitored on the mobile device 166-2 for an extended period of time, where real-time video is displayed to the user. This can be done to enhance the emotional connection between the user and the infant through the mobile device 166-2. For example, a parent who needs to be away from the infant during the day can log into the server 164 using the mobile device 166-2 and watch real-time video of the infant.

In some cases, the user can monitor the infant to watch for medical conditions such as sleep apnea, pauses or disruptions in breathing, abnormal heartbeats, seizures, and so forth. While normal video streams of previous systems in the art would make it difficult or impossible to visually see or detect these medical conditions, the camera system and exaggerated representations described below can make these medical conditions readily apparent to an observer of the mobile device 166-2. In some embodiments, the displacement maps formed by the pixels 904 can be compared to known frequencies or other motion signatures to identify specific medical conditions such as those listed above. For example, a rapid and small movement frequency may be identified in the pixels 904 in each frame and matched to a signature that indicates a seizure is taking place. In another example, if the pixel displacements in the pixels 904 do not show a change in displacement for a predetermined number of successive frames, this may indicate a pause in breathing and/or heartbeat that can indicate a serious medical condition. In addition to simply displaying the real-time video feed 1002, the mobile device 166-2 can also display visual/audio warnings or status messages for any of the medical conditions detected above. For example, a pause in breathing can cause the mobile device 166-2 to display a warning and produce an alarm sound to alert the user.

In some embodiments, the detection of abnormal medical conditions may be exceedingly rare and not the primary purpose of monitoring the infant 602. For example, a parent may simply wish to watch their infant sleep. Seeing the animated motion of the infant's breathing can enhance the emotional connection the parent may have with the infant 602. Because these breathing motions and heartbeat motions are typically too small to be recorded by a monitoring camera and displayed on a mobile device 166-2, the methods described herein may present an exaggerated representation of these vital signs. In some embodiments, the pixel displacements in the pixels 904 can be multiplied by a scale factor. For example, in FIG. 11, the displacements in the pixels 904 have been multiplied by a factor of "2." Instead of a peak displacement of "3" pixels at the center of the chest of the infant, the peak displacement has been doubled to be a displacement of "6" pixels. Any displacement factor may be used, such as 1.1, 1.2, 1.5, 1.7, 2.0, 2.5, 3.0, 5.0 and so forth.

Figure 12A:
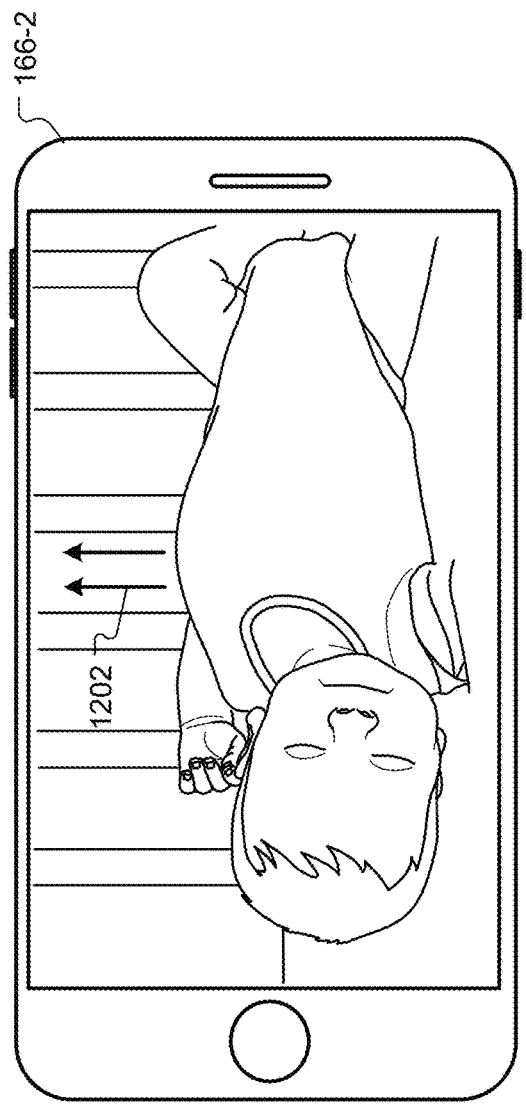
FIG. 12A illustrates the peak breathing position represented by the pixel displacements after being scaled by a factor, according to some embodiments.

By scaling the displacement of each pixel, an exaggerated representation of the monitored vital signs can be presented on the mobile device 166-2. FIG. 12A illustrates the peak breathing position represented by the pixel displacements 904 after being scaled by a factor of "2" according to some embodiments. Each pixel for which motion was detected in the actual video feed has been multiplied by a scale factor such that the motion can be exaggerated in the video that is played on the mobile device 166-2. For example, a pixel that was originally displaced by 3 pixels would now be displaced by 6 pixels in FIG. 12A. Thus, the chest of the infant would appear to rise twice as far as it did in the actual video feed received from the camera. Each pixel in the video sequence displayed on the mobile device 166-2 can have this warping effect performed using the exaggerated pixel displacement distances calculated above. The motion 1202 displayed on the mobile device 166-2 will now be large enough such that it is easily visible on the small screen of the mobile device 166-2. This can be contrasted with how such motion would normally be impossible to visually detect on the mobile device 166-2 without the exaggeration provided by this system.

Figure 12B:
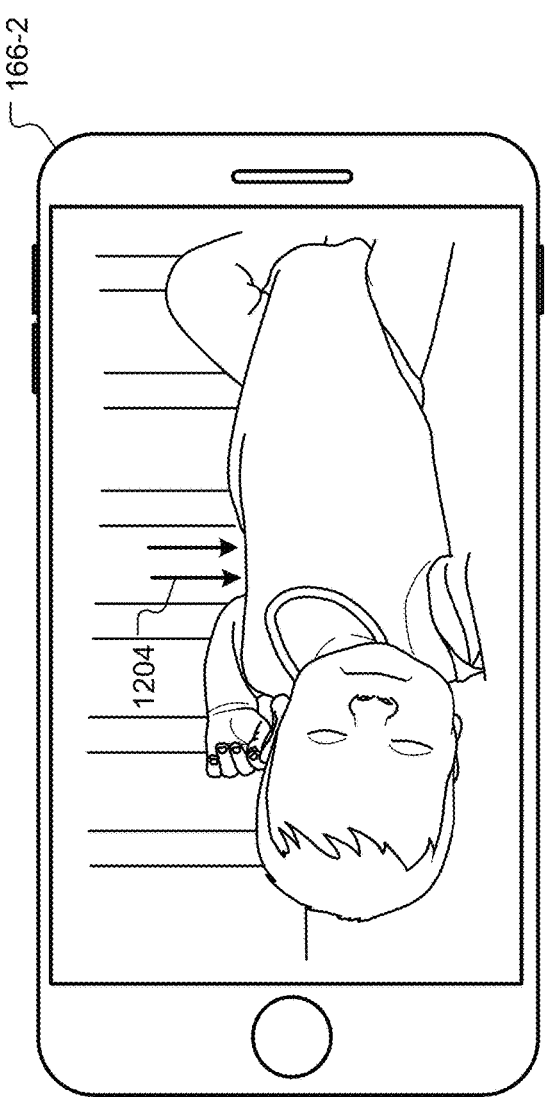
FIG. 12B illustrates a subsequent frame in the video sequence that is rendered and displayed on the mobile device, according to some embodiments.

FIG. 12B illustrates a subsequent frame in the video sequence that is rendered and displayed on the mobile device 166-2, according to some embodiments. In embodiments where the baseline position of the motion represents an average chest position, then displacements as the infant exhales may have a negative magnitude in the breathing direction. When these displacements are scaled, these displacements will tend to become more negative. When those displacements are applied to the pixels in the video sequence displayed on the mobile device 166-2, the exhaling of the infant will also become more exaggerated in the motion 1204 on the mobile device 166-2. For example, the chest will tend to sink in farther on the video. When the exaggerated exhale is combined with the exaggerated inhale, the breathing of the infant becomes very pronounced and easy to visually follow on the mobile device 166-2.

Although the examples above deal with a breathing pattern of the infant, this can also apply to any other small motions that are detected by the camera 118. The size of these small motions can determine the size of the scaling factor used when generating the exaggerated representation on the mobile device 166-2. For example, the motions that can be attributed to a heartbeat may be very small, and a corresponding scaling factor of 5 to 7 can be used to make such small motions visible on the mobile device 166-2. The sucking of a pacifier may be fairly pronounced compared to that of a heartbeat, and thus the scaling factor of 1.5 can be used so that the exaggerated motion does not appear too unrealistic.

Figure 13B:
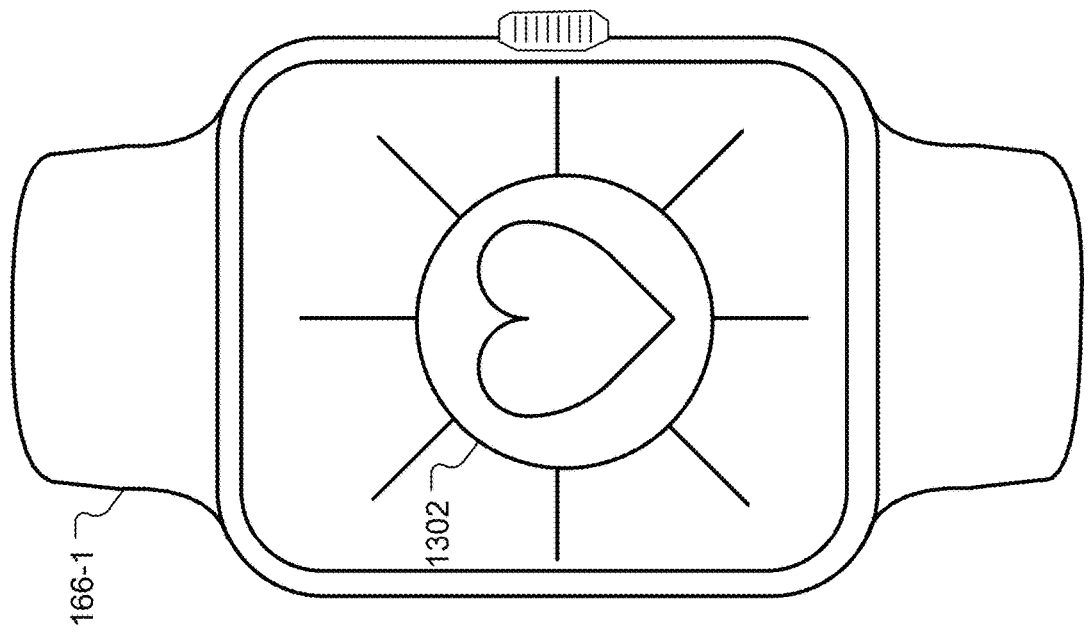
FIG. 13B illustrates an alternative visual representation of a vital sign on a mobile device, according to some embodiments.
Figure 13A:
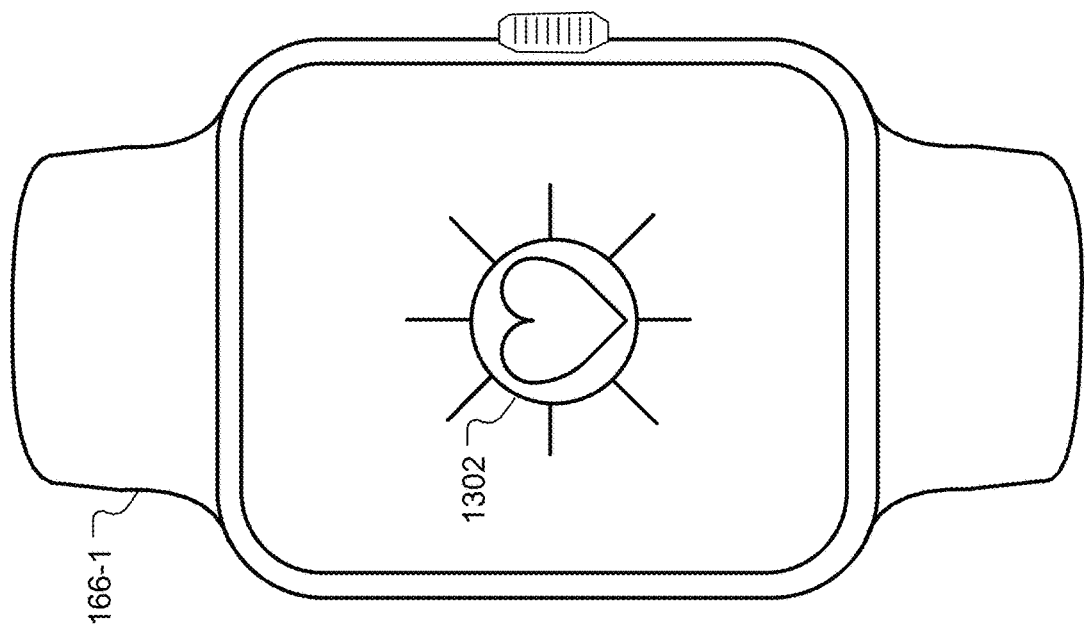
FIG. 13A illustrates an alternative visual representation of a vital sign on a mobile device, according to some embodiments.

FIG. 13A and FIG. 13B illustrate an alternative visual representation of a vital sign on a mobile device 166-1, according to some embodiments. In this embodiment, the mobile device 166-1 may include a smart watch or other piece of wearable technology. In some embodiments, the live or exaggerated video stream can be also displayed on the mobile device 166-1. Additionally or alternatively, animations or other visual indicators can be used to represent the vital sign(s) monitored and detected by the camera 118. In this example, a pulsating graphic 1302 can be used to display the timing and magnitude of the breathing, heart rate, etc., of the monitored subject. The calculated pixel displacements from the live video feed can be averaged together to generate a single displacement magnitude for each frame. That single displacement can then be used to drive the animation of the graphic 1302 on the mobile device 166-1. For example, the graphic 1302 can pulsate visually with each heartbeat of the monitored subject. The graphic 1302 can also pulsate visually with each breath taken by the monitored subject. In some embodiments, this pulsation can be exaggerated by scaling the displacement as described above. This motion can also be normalized such that a full heartbeat/breath causes the graphic 1302 to substantially fill the screen (e.g., filling more than 50% of the screen of the mobile device 166-1). Motion can also be normalized such that a pause between heartbeats or breaths causes the graphic 1302 to be a predetermined minimum size on the screen of the mobile device 166-1.

The graphic 1302 illustrated in FIG. 13A and FIG. 13B is provided merely by example and not meant to be limiting. Many other types of graphics may be used including pulsating status bars, animated heartbeats, simulated breathing animations, animated characters or avatars performing the vital signs being monitored, and so forth. These graphics may also be mixed with the live video feed. For example, the live video feed may display the live or exaggerated motion of the monitored subject, while a graphic simultaneously is animated in the corner of the screen to illustrate or accentuate the small motions detected by the cameras that are indicative of the monitored vital sign. In some embodiments, the graphic can also be superimposed over the image of the monitored subject in live video feed. For example, the graphic 1302 can be superimposed on top of the visual location of an infant's heart in the live video feed.

Figure 14:
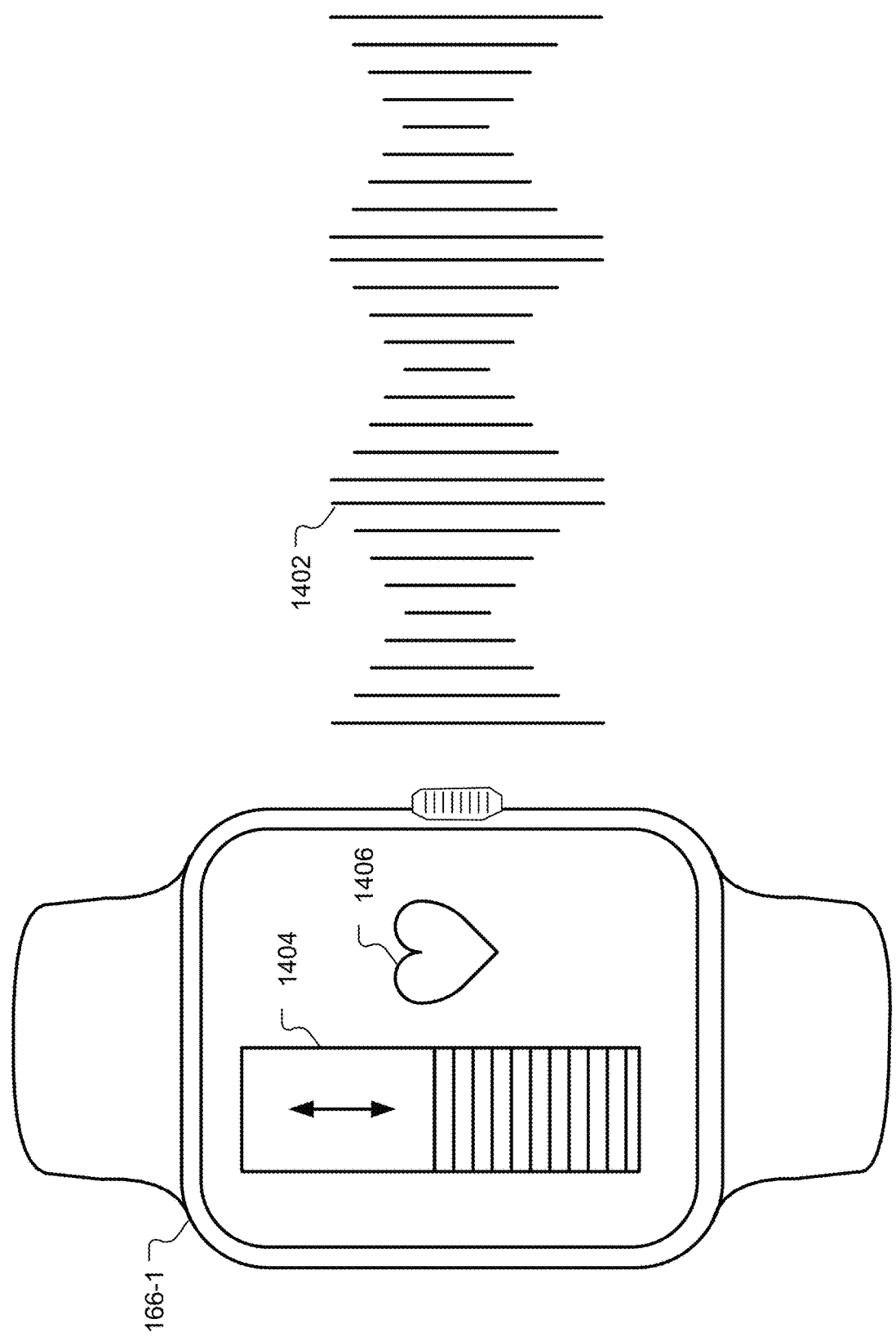
FIG. 14 illustrates additional representations of motion that may be provided through a mobile device, according to some embodiments.

FIG. 14 illustrates additional representations of motion that may be provided through a mobile device 166-1, according to some embodiments. In this example, the mobile device 166-1 may include graphics 1404, 1406 that are animated and driven by the displacements calculated from the live video feed. The mobile device 166-1 may also additionally or alternatively display the exaggerated or un-exaggerated live video feed of the subject being monitored. The live video feed may be combined with the graphics 1404, 1406 as described above. In addition to these visual indicators that may be displayed by the mobile device 166-1, the presentation of a representation of the motion detected by the camera may also include non-graphical indicators. For example, the mobile device 166-1 can emit an audio signal 1402 that is driven by the pixel displacements in the video feed. The average displacement of all the pixels can be used to drive a simulated breathing sound or heartbeat sound that can be audibly emitted by the mobile device 166-1 through a speaker.

Just as the pixel displacements were scaled by a factor in the live video feed to exaggerate the visual motion, any rhythmic breathing that is audibly detected by the microphone on the camera 118 can also be reproduced and/or exaggerated. For example, a breathing sound detected by the camera can be transmitted to the mobile device 166-1. Each sample in the soundwave can be compared to a baseline value and a displacement from that baseline value can be calculated. The displacement values can be scaled to exaggerate the sound, and the sound can thus be exaggerated as described above for video pixels. The exaggerated sound can then be emitted by the mobile device 166-1.

In some embodiments, the mobile device 166-1 may additionally or alternatively emit a vibration with a magnitude and timing that are determined by the displacement value calculated from the video sequence. Many mobile devices come equipped with a vibration device that can cause the device to vibrate when a call is received, when an alarm is triggered, etc. This vibration device in the mobile device 166-1 can be driven in terms of timing and intensity by the displacement values from the vital sign monitored by the camera 118. This may allow a user to monitor a vital sign without being required to visually watch the screen of the mobile device 166-1. For example, a user can monitor a vital sign with their smart watch on their wrist, or with their phone in their pocket while they drive or walk without being visually distracted by a live video feed.

Figure 15:
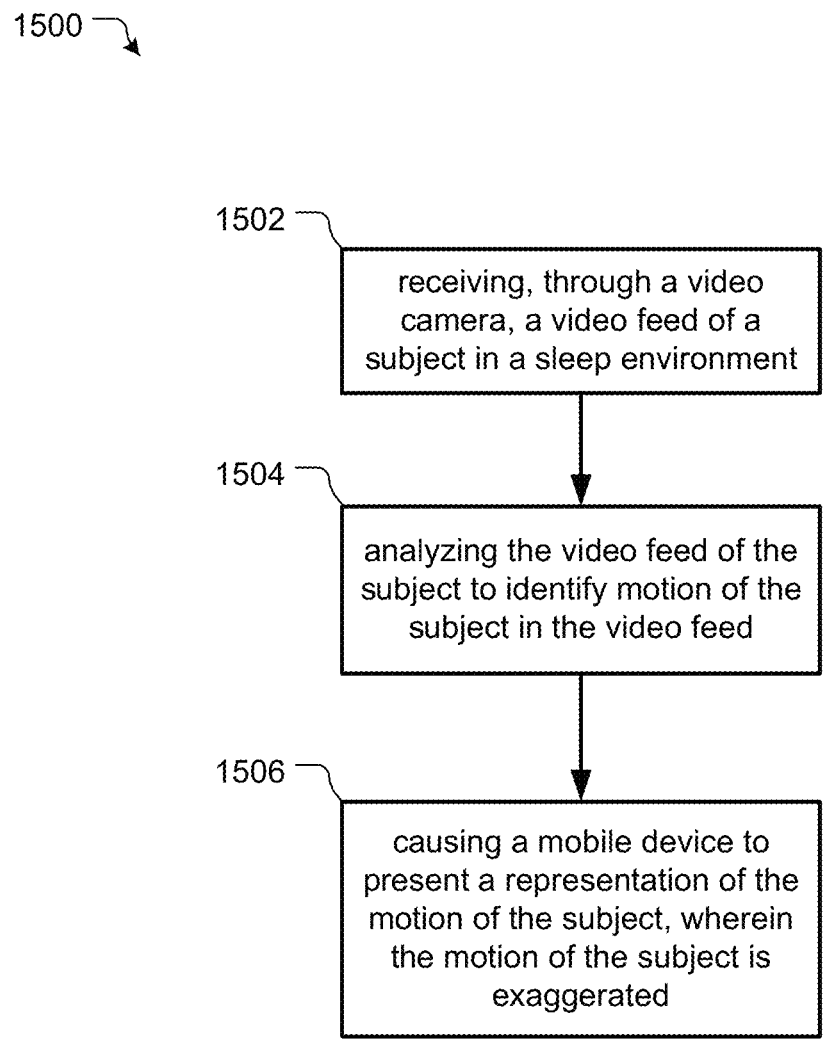
FIG. 15 illustrates a simplified flowchart of a method for monitoring physical characteristics of subjects in sleep environments.

FIG. 15 illustrates a simplified flowchart 1500 of a method for monitoring physical characteristics of subjects in sleep environments. The method may include receiving, through a video camera, a video feed of a subject in a sleep environment (1502). The subject may include an infant, an elderly individual, or any other individual requiring monitoring. The method may further include analyzing a video feed of the subject to identify motion of the subject in the video feed (1504). The video feed may be analyzed by the video camera, a remote server, or at a mobile device. The area analyzed in a video feed may be reduced to a bounding box or area around the subject, and large motions above a threshold may be filtered from the analysis. The identified motion may be represented using motion vectors or pixel displacements in a displacement image. The method may additionally include causing a mobile device to present a representation of the motion of the subject (1506). In some embodiments, the motion of the subject may be exaggerated. The representation of motion of the subject presented may include video feeds, exaggerated video feeds, audio simulations, audio feeds, graphic animations, device vibrations, and so forth.

It should be appreciated that the specific steps illustrated in FIG. 15 provide particular methods of monitoring physical characteristics of subjects in sleep environments according to various embodiments of the present invention. Other sequences of steps may also be performed according to alternative embodiments. For example, alternative embodiments of the present invention may perform the steps outlined above in a different order. Moreover, the individual steps illustrated in FIG. 15 may include multiple sub-steps that may be performed in various sequences as appropriate to the individual step. Furthermore, additional steps may be added or removed depending on the particular applications. One of ordinary skill in the art would recognize many variations, modifications, and alternatives.

In the foregoing description, for the purposes of explanation, numerous specific details were set forth in order to provide a thorough understanding of various embodiments of the present invention. It will be apparent, however, to one skilled in the art that embodiments of the present invention may be practiced without some of these specific details. In other instances, well-known structures and devices are shown in block diagram form.

The foregoing description provides exemplary embodiments only, and is not intended to limit the scope, applicability, or configuration of the disclosure. Rather, the foregoing description of the exemplary embodiments will provide those skilled in the art with an enabling description for implementing an exemplary embodiment. It should be understood that various changes may be made in the function and arrangement of elements without departing from the spirit and scope of the invention as set forth in the appended claims.

Specific details are given in the foregoing description to provide a thorough understanding of the embodiments. However, it will be understood by one of ordinary skill in the art that the embodiments may be practiced without these specific details. For example, circuits, systems, networks, processes, and other components may have been shown as components in block diagram form in order not to obscure the embodiments in unnecessary detail. In other instances, well-known circuits, processes, algorithms, structures, and techniques may have been shown without unnecessary detail in order to avoid obscuring the embodiments.

Also, it is noted that individual embodiments may have been described as a process which is depicted as a flowchart, a flow diagram, a data flow diagram, a structure diagram, or a block diagram. Although a flowchart may have described the operations as a sequential process, many of the operations can be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function.

The term "computer-readable medium" includes, but is not limited to portable or fixed storage devices, optical storage devices, wireless channels and various other mediums capable of storing, containing, or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc., may be passed, forwarded, or transmitted via any suitable means including memory sharing, message passing, token passing, network transmission, etc.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

In the foregoing specification, aspects of the invention are described with reference to specific embodiments thereof, but those skilled in the art will recognize that the invention is not limited thereto. Various features and aspects of the above-described invention may be used individually or jointly. Further, embodiments can be utilized in any number of environments and applications beyond those described herein without departing from the broader spirit and scope of the specification. The specification and drawings are, accordingly, to be regarded as illustrative rather than restrictive.

Additionally, for the purposes of illustration, methods were described in a particular order. It should be appreciated that in alternate embodiments, the methods may be performed in a different order than that described. It should also be appreciated that the methods described above may be performed by hardware components or may be embodied in sequences of machine-executable instructions, which may be used to cause a machine, such as a general-purpose or special-purpose processor or logic circuits programmed with the instructions to perform the methods. These machine-executable instructions may be stored on one or more machine readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

What is claimed is:

1. A method of monitoring physical characteristics of subjects in sleep environments, the method comprising: receiving, through a video camera, a video feed of a subject in a sleep environment; analyzing the video feed of the subject to identify motion of the subject in the video feed that is below a threshold amount of motion; generating a displacement map for pixels moving below the threshold amount of motion, wherein the displacement map comprises values indicating a distance by which the pixels in a previous frame have moved in relation to a current frame; and causing a mobile device to present a representation of the motion of the subject, wherein the motion of the subject that is below the threshold amount of motion is exaggerated by: scaling the values in the displacement map; altering pixel locations in the video feed based on the displacement map after scaling the values in the displacement map; and displaying the pixels with altered locations in an overlaid fashion in the video feed.

2. The method of claim 1, wherein analyzing the video feed of the subject to identify motion of the subject in the video feed comprises identifying motions of the subject that are repeated.

3. The method of claim 1, wherein analyzing the video feed of the subject to identify the motion of the subject in the video feed comprises analyzing the video feed of the subject to identify motion of the subject in the video feed comprises identifying motions of the subject that are repeated and less than a threshold amount of motion.

4. The method of claim 1, wherein analyzing the video feed further comprises identifying an area in a field-of-view of the camera that includes the motion of the subject.

5. The method of claim 4, wherein analyzing the video feed further comprises reducing a resolution of the video feed outside of the area.

6. The method of claim 1, wherein the motion of the subject in the video feed comprises a rhythmic breathing motion.

7. The method of claim 1, wherein the motion of the subject in the video feed comprises a chest rising and falling with a heartbeat of the subject.

8. A system for monitoring physical characteristics of subjects in sleep environments, the system comprising: a video camera; one or more processors; and one or more memory devices comprising instructions that, when executed by the one or more processors, cause the one or more processors to perform operations comprising: receiving, through a video camera, a video feed of a subject in a sleep environment; analyzing the video feed of the subject to identify motion of the subject in the video feed that is below a threshold amount of motion; generating a displacement map for pixels moving below the threshold amount of motion, wherein the displacement map comprises values indicating a distance by which the pixels in a previous frame have moved in relation to a current frame; and causing a mobile device to present a representation of the motion of the subject, wherein the motion of the subject that is below the threshold amount of motion is exaggerated by: scaling the values in the displacement map; altering pixel locations in the video feed based on the displacement map after scaling the values in the displacement map; and displaying the pixels with altered locations in an overlaid fashion in the video feed.

9. The system of claim 8, wherein the mobile device comprises a smart phone.

10. The system of claim 8, further comprising a monitor server, wherein the one or more processors are at least partially located at the monitor server.

11. The system of claim 8, wherein the representation of the motion of the subject comprises a pulsating graphic to be displayed on the mobile device where the pulsating is based on a timing of the motion of the subject.

12. The system of claim 8, wherein the representation of the motion of the subject comprises a rhythmic audio output that is based on a timing of the motion of the subject.

13. The system of claim 8, wherein analyzing the video feed of the subject to identify motion of the subject in the video feed comprises identifying motions of the subject that are repeated.

14. The system of claim 8, wherein analyzing the video feed of the subject to identify the motion of the subject in the video feed comprises filtering motions that are larger than a threshold amount of motion or which are not repeated.

15. The system of claim 8, wherein analyzing the video feed further comprises identifying an area in a field-of-view of the camera that includes the motion of the subject.

16. The system of claim 15, wherein analyzing the video feed further comprises reducing a resolution of the video feed outside of the area.

* * * * *